US009428800B2

(12) United States Patent
Linton et al.

(10) Patent No.: US 9,428,800 B2
(45) Date of Patent: Aug. 30, 2016

(54) THERMAL CYCLING APPARATUS AND METHOD

(71) Applicant: LIFE TECHNOLOGIES CORPORATION, Carlsbad, CA (US)

(72) Inventors: John Linton, Lincoln, MA (US); Arrin Katz, Cambridge, MA (US); Colin Brenan, Marblehead, MA (US); Karl Yoder, Stoneham, MA (US); Robert Hess, Arlington, MA (US); Leila Madrone, San Francisco, CA (US); Robert Ellis, Half Moon Bay, CA (US); Tanya Kanigan, Winchester, MA (US); Kristine Friesen, Cambridge, MA (US); Thomas Morrison, Wilmington, NC (US); Javier Garcia, Lexington, MA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/195,358

(22) Filed: Mar. 3, 2014

(65) Prior Publication Data
US 2014/0179566 A1 Jun. 26, 2014

Related U.S. Application Data

(60) Continuation of application No. 13/491,989, filed on Jun. 8, 2012, now Pat. No. 8,697,452, which is a
(Continued)

(51) Int. Cl.
G01N 31/22 (2006.01)
G01N 21/01 (2006.01)
(Continued)

(52) U.S. Cl.
CPC ............ *C12Q 1/6858* (2013.01); *B01L 3/508* (2013.01); *B01L 3/5025* (2013.01);
(Continued)

(58) Field of Classification Search
USPC .................... 436/43, 86, 164–166, 180, 805, 436/171–172, 147; 435/6.12, 6.1, 6.11; 422/67, 68.1
See application file for complete search history.

(56) References Cited

U.S. PATENT DOCUMENTS

| 1,236,137 A | 8/1917 | Bastow |
| 2,745,001 A | 5/1956 | Guth |

(Continued)

FOREIGN PATENT DOCUMENTS

| DE | 10046224 | 3/2002 |
| EP | 65643 | 12/1982 |

(Continued)

OTHER PUBLICATIONS 6814869.1, "Extended European Search Report Mailed Oct. 18, 2010", 7.
(Continued)

*Primary Examiner* — Brian R Gordon

(57) ABSTRACT

A system for holding at least one of sample and reagent for analysis. The system includes a pair of parallel covers, at least one of which is light transmissive, of which pair a light transmissive cover forms a top, and of which pair the other forms a bottom. A frame is disposed between the covers to define, in relation to the covers, an interior volume. The frame and the covers are associated with one another to form a case, the case being substantially tight to liquids. A microfluidic array is disposed in the interior volume. The array includes a sheet of material having a pair of opposed surfaces, a thickness, and a plurality of through-holes running through the thickness between the surfaces, the through-holes containing at least one of sample and reagent.

9 Claims, 15 Drawing Sheets

Related U.S. Application Data continuation of application No. 12/243,503, filed on Oct. 1, 2008, now abandoned, which is a division of application No. 10/744,580, filed on Dec. 22, 2003, now Pat. No. 7,682,565.

(60) Provisional application No. 60/528,461, filed on Dec. 10, 2003, provisional application No. 60/461,556, filed on Apr. 9, 2003, provisional application No. 60/461,559, filed on Apr. 9, 2003, provisional application No. 60/434,988, filed on Dec. 20, 2002.

(51) Int. Cl.
| | |
|---|---|
| G01N 21/77 | (2006.01) |
| C12Q 1/68 | (2006.01) |
| B01L 3/00 | (2006.01) |
| G01N 21/03 | (2006.01) |
| G01N 21/15 | (2006.01) |
| G01N 21/25 | (2006.01) |
| B01L 7/00 | (2006.01) |
| G01N 21/05 | (2006.01) |

(52) U.S. Cl.
CPC .......... *B01L 3/50857* (2013.01); *G01N 21/03* (2013.01); *G01N 21/15* (2013.01); *G01N 21/253* (2013.01); *B01L 3/5027* (2013.01); *B01L 3/50853* (2013.01); *B01L 7/52* (2013.01); *B01L 2200/16* (2013.01); *B01L 2300/021* (2013.01); *B01L 2300/0609* (2013.01); *B01L 2300/0636* (2013.01); *B01L 2300/0819* (2013.01); *B01L 2300/0829* (2013.01); *B01L 2300/16* (2013.01); *B01L 2300/1822* (2013.01); *B01L 2300/1838* (2013.01); *G01N 2021/0346* (2013.01); *G01N 2021/056* (2013.01); *G01N 2021/158* (2013.01); *Y10T 436/11* (2015.01); *Y10T 436/25* (2015.01); *Y10T 436/2575* (2015.01)

(56) References Cited

U.S. PATENT DOCUMENTS

| | | |
|---|---|---|
| 2,771,398 A | 11/1956 | Snyder |
| 3,043,669 A | 7/1962 | Charles |
| 3,170,980 A | 2/1965 | Pritchard |
| 3,252,331 A | 5/1966 | Lancaster |
| 3,768,974 A | 10/1973 | Storm |
| 3,770,383 A | 11/1973 | Price |
| 3,864,512 A | 2/1975 | Meadow |
| 3,873,268 A | 3/1975 | McKie |
| 3,894,512 A | 7/1975 | Ohno |
| 3,997,396 A | 12/1976 | Delente |
| 4,007,010 A | 2/1977 | Woodbridge et al. |
| 4,065,263 A | 12/1977 | Woodbridge |
| 4,088,448 A | 5/1978 | Lilja et al. |
| 4,110,165 A | 8/1978 | Cole et al. |
| 4,111,754 A | 9/1978 | Park |
| 4,234,316 A | 11/1980 | Hevey |
| 4,273,877 A | 6/1981 | Anagnostopoulos |
| 4,415,732 A | 11/1983 | Caruthers et al. |
| 4,446,239 A | 5/1984 | Tsuji |
| 4,453,805 A | 6/1984 | Ashkin et al. |
| 4,458,066 A | 7/1984 | Caruthers et al. |
| 4,493,815 A | 1/1985 | Fernwood et al. |
| 4,500,707 A | 2/1985 | Caruthers et al. |
| 4,562,045 A | 12/1985 | Murata |
| 4,562,871 A | 1/1986 | Astle |
| 4,586,546 A | 5/1986 | Mezei et al. |
| 4,613,573 A | 9/1986 | Shibayama et al. |
| 4,626,509 A | 12/1986 | Lyman |
| 4,659,677 A | 4/1987 | Glover et al. |
| 4,663,163 A | 5/1987 | Hou et al. |
| 4,678,894 A | 7/1987 | Shafer |
| 4,682,890 A | 7/1987 | de Macario et al. |
| 4,682,891 A | 7/1987 | de Macario et al. |
| 4,683,195 A | 7/1987 | Mullis et al. |
| 4,683,202 A | 7/1987 | Mullis |
| 4,701,304 A | 10/1987 | Horn et al. |
| 4,722,515 A | 2/1988 | Ham |
| 4,734,192 A | 3/1988 | Champion et al. |
| 4,761,378 A | 8/1988 | Godsey |
| 4,828,386 A | 5/1989 | Matkovich et al. |
| 4,834,946 A | 5/1989 | Levin |
| 4,861,448 A | 8/1989 | Cantor et al. |
| 4,861,722 A | 8/1989 | Sano et al. |
| 4,869,114 A | 9/1989 | Kido et al. |
| 4,873,633 A | 10/1989 | Mezei et al. |
| 4,893,886 A | 1/1990 | Ashkin et al. |
| 4,932,806 A | 6/1990 | Eklund et al. |
| 4,965,188 A | 10/1990 | Mullis et al. |
| 4,973,679 A | 11/1990 | Caruthers et al. |
| 4,990,459 A | 2/1991 | Maeda et al. |
| 5,000,921 A | 3/1991 | Hanaway et al. |
| 5,009,846 A | 4/1991 | Gavet et al. |
| 5,038,852 A | 8/1991 | Johnson et al. |
| 5,041,266 A | 8/1991 | Fox |
| 5,047,215 A | 9/1991 | Manns |
| 5,100,627 A | 3/1992 | Buican et al. |
| 5,108,704 A | 4/1992 | Bowers et al. |
| 5,108,926 A | 4/1992 | Klebe |
| 5,152,060 A | 10/1992 | Schubert et al. |
| 5,153,319 A | 10/1992 | Caruthers et al. |
| 5,175,209 A | 12/1992 | Beattie et al. |
| 5,185,243 A | 2/1993 | Ullman et al. |
| 5,192,980 A | 3/1993 | Dixon et al. |
| 5,204,268 A | 4/1993 | Matsumoto |
| 5,210,021 A | 5/1993 | Goodwin, Jr. |
| 5,215,593 A | 6/1993 | Nojo et al. |
| 5,219,727 A | 6/1993 | Wang et al. |
| 5,229,163 A | 7/1993 | Fox |
| 5,234,665 A | 8/1993 | Ohta et al. |
| 5,234,666 A | 8/1993 | Suzuki |
| 5,242,794 A | 9/1993 | Whiteley et al. |
| 5,242,974 A | 9/1993 | Holmes |
| 5,262,128 A | 11/1993 | Leighton et al. |
| 5,284,753 A | 2/1994 | Goodwin, Jr. |
| 5,290,705 A | 3/1994 | Davis |
| 5,310,652 A | 5/1994 | Gelfand et al. |
| 5,322,019 A | 6/1994 | Hyland |
| 5,322,770 A | 6/1994 | Gelfand |
| 5,333,675 A | 8/1994 | Mullis et al. |
| 5,373,803 A | 12/1994 | Noguchi et al. |
| 5,374,525 A | 12/1994 | Lalouel et al. |
| 5,382,985 A | 1/1995 | Becker et al. |
| 5,407,800 A | 4/1995 | Gelfand et al. |
| 5,411,876 A | 5/1995 | Bloch et al. |
| 5,427,908 A | 6/1995 | Dower et al. |
| 5,433,975 A | 7/1995 | Roberts et al. |
| 5,443,791 A | 8/1995 | Cathcart et al. |
| 5,445,934 A | 8/1995 | Fodor et al. |
| 5,453,252 A | 9/1995 | Truett |
| 5,455,008 A | 10/1995 | Earley et al. |
| 5,466,583 A | 11/1995 | Thomson et al. |
| 5,466,603 A | 11/1995 | Meehan et al. |
| 5,475,610 A | 12/1995 | Atwood et al. |
| 5,476,744 A | 12/1995 | Anno |
| 5,476,774 A | 12/1995 | Wang et al. |
| 5,491,083 A | 2/1996 | Arentzen et al. |
| 5,492,806 A | 2/1996 | Drmanac et al. |
| 5,504,007 A | 4/1996 | Haynes |
| 5,506,141 A | 4/1996 | Weinreb et al. |
| 5,508,197 A | 4/1996 | Hansen et al. |
| 5,508,200 A | 4/1996 | Tiffany et al. |
| 5,510,270 A | 4/1996 | Fodor et al. |
| 5,516,641 A | 5/1996 | Ullman et al. |
| 5,519,218 A | 5/1996 | Chang |
| 5,525,464 A | 6/1996 | Drmanac et al. |
| 5,538,848 A | 7/1996 | Livak et al. |
| 5,554,339 A | 9/1996 | Cozzette et al. |
| 5,560,811 A | 10/1996 | Briggs et al. |
| 5,561,058 A | 10/1996 | Gelfand et al. |

(56) References Cited

U.S. PATENT DOCUMENTS

| | | |
|---|---|---|
| 5,561,071 A | 10/1996 | Hollenberg et al. |
| 5,576,220 A | 11/1996 | Hudson et al. |
| 5,580,717 A | 12/1996 | Dower et al. |
| 5,585,275 A | 12/1996 | Hudson et al. |
| 5,589,136 A | 12/1996 | Northrup et al. |
| 5,593,839 A | 1/1997 | Hubbell et al. |
| 5,593,840 A | 1/1997 | Bhatnagar et al. |
| 5,599,664 A | 2/1997 | Schwartz |
| 5,602,756 A | 2/1997 | Atwood et al. |
| 5,605,662 A | 2/1997 | Heller et al. |
| 5,609,828 A | 3/1997 | O'Bear et al. |
| 5,616,301 A | 4/1997 | Moser et al. |
| 5,621,094 A | 4/1997 | Roser et al. |
| 5,632,957 A | 5/1997 | Heller et al. |
| 5,641,391 A | 6/1997 | Hunter et al. |
| 5,641,864 A | 6/1997 | Gelfand |
| 5,656,493 A | 8/1997 | Mullis et al. |
| 5,667,972 A | 9/1997 | Drmanac et al. |
| 5,670,329 A | 9/1997 | Oberhardt |
| 5,710,381 A | 1/1998 | Atwood et al. |
| 5,720,923 A | 2/1998 | Haff et al. |
| 5,722,370 A | 3/1998 | Koike et al. |
| 5,744,101 A | 4/1998 | Fodor et al. |
| 5,763,263 A | 6/1998 | Dehlinger et al. |
| 5,770,440 A | 6/1998 | Berndt |
| 5,770,441 A | 6/1998 | Lipton |
| 5,770,860 A | 6/1998 | Franzen |
| 5,773,238 A | 6/1998 | Shukla |
| 5,780,233 A | 7/1998 | Guo et al. |
| 5,785,926 A | 7/1998 | Seubert et al. |
| 5,786,226 A | 7/1998 | Bocker et al. |
| 5,795,748 A | 8/1998 | Cottingham et al. |
| 5,807,522 A | 9/1998 | Brown et al. |
| 5,814,524 A | 9/1998 | Walt et al. |
| 5,840,862 A | 11/1998 | Bensimon et al. |
| 5,843,767 A | 12/1998 | Beattie et al. |
| 5,849,598 A | 12/1998 | Wilson et al. |
| 5,856,100 A | 1/1999 | Hayashizaki |
| 5,869,006 A | 2/1999 | Fanning et al. |
| 5,871,908 A | 2/1999 | Henco et al. |
| 5,879,632 A | 3/1999 | Demers |
| 5,888,723 A | 3/1999 | Sutton et al. |
| 5,897,842 A | 4/1999 | Dunn et al. |
| 5,906,683 A | 5/1999 | Chen et al. |
| 5,910,287 A | 6/1999 | Cassin et al. |
| 5,922,604 A | 7/1999 | Stapleton et al. |
| 5,928,907 A | 7/1999 | Woudenberg et al. |
| 5,929,208 A | 7/1999 | Heller et al. |
| 5,942,432 A | 8/1999 | Smith et al. |
| 5,944,652 A | 8/1999 | Miller et al. |
| 5,955,377 A | 9/1999 | Maul et al. |
| 5,958,345 A | 9/1999 | Turner et al. |
| 5,962,316 A | 10/1999 | Beach et al. |
| 5,985,214 A | 11/1999 | Stylli et al. |
| 5,994,056 A | 11/1999 | Higuchi |
| 6,001,586 A | 12/1999 | Schellenberger et al. |
| 6,004,744 A | 12/1999 | Goelet et al. |
| 6,015,880 A | 1/2000 | Baldeschwieler et al. |
| 6,020,141 A | 2/2000 | Pantoliano et al. |
| 6,024,925 A | 2/2000 | Little et al. |
| 6,027,873 A | 2/2000 | Schellenberger et al. |
| 6,027,889 A | 2/2000 | Barany et al. |
| 6,060,240 A | 5/2000 | Kamb et al. |
| 6,071,702 A | 6/2000 | Yamamoto et al. |
| 6,071,748 A | 6/2000 | Modlin et al. |
| 6,083,682 A | 7/2000 | Campbell et al. |
| 6,083,763 A | 7/2000 | Balch |
| 6,086,825 A | 7/2000 | Sundberg et al. |
| 6,088,100 A | 7/2000 | Brenan et al. |
| 6,090,251 A | 7/2000 | Sundberg et al. |
| 6,103,199 A | 8/2000 | Bjornson et al. |
| 6,103,479 A | 8/2000 | Taylor |
| 6,107,059 A | 8/2000 | Hart |
| 6,121,048 A | 9/2000 | Zaffaroni et al. |
| 6,132,685 A | 10/2000 | Kercso et al. |
| 6,136,566 A | 10/2000 | Sands et al. |
| 6,136,592 A | 10/2000 | Leighton |
| H1919 H | 11/2000 | Caspar et al. |
| 6,147,198 A | 11/2000 | Schwartz |
| 6,149,787 A | 11/2000 | Chow et al. |
| 6,149,815 A | 11/2000 | Sauter |
| 6,174,670 B1 | 1/2001 | Wittwer et al. |
| 6,197,563 B1 | 3/2001 | Erlich et al. |
| 6,207,031 B1 | 3/2001 | Adourian et al. |
| 6,215,894 B1 | 4/2001 | Zeleny et al. |
| 6,235,473 B1 | 5/2001 | Friedman et al. |
| 6,245,505 B1 | 6/2001 | Todd et al. |
| 6,251,343 B1 | 6/2001 | Dubrow et al. |
| 6,271,024 B1 | 8/2001 | Sve et al. |
| 6,274,089 B1 | 8/2001 | Chow et al. |
| 6,284,113 B1 | 9/2001 | Bjornson et al. |
| 6,296,702 B1 | 10/2001 | Bryning et al. |
| 6,306,578 B1 | 10/2001 | Schellenberger et al. |
| 6,309,600 B1 | 10/2001 | Hunter |
| 6,309,828 B1 | 10/2001 | Schleifer et al. |
| 6,312,103 B1 | 11/2001 | Haluzak |
| 6,326,083 B1 | 12/2001 | Yang et al. |
| 6,337,435 B1 | 1/2002 | Chu et al. |
| 6,353,774 B1 | 3/2002 | Goldenberg et al. |
| 6,376,256 B1 | 4/2002 | Dunnington et al. |
| 6,387,331 B1 | 5/2002 | Hunter |
| 6,391,559 B1 | 5/2002 | Brown et al. |
| 6,399,396 B1 | 6/2002 | Bass |
| 6,399,952 B1 | 6/2002 | Maher et al. |
| 6,404,166 B1 | 6/2002 | Puchianu |
| 6,406,869 B1 | 6/2002 | Glickman et al. |
| 6,410,331 B1 | 6/2002 | Schultz et al. |
| 6,429,025 B1 | 8/2002 | Parce et al. |
| 6,436,632 B2 | 8/2002 | Schellenberger et al. |
| 6,447,661 B1 | 9/2002 | Chow et al. |
| 6,451,188 B1 | 9/2002 | Sundberg et al. |
| 6,454,924 B2 | 9/2002 | Jedrzejewski et al. |
| 6,468,761 B2 | 10/2002 | Yang et al. |
| 6,485,690 B1 | 11/2002 | Pfost et al. |
| 6,485,944 B1 | 11/2002 | Church et al. |
| 6,495,104 B1 | 12/2002 | Unno et al. |
| 6,495,369 B1 | 12/2002 | Kercso et al. |
| 6,503,757 B1 | 1/2003 | Chow |
| 6,509,059 B2 | 1/2003 | Yang et al. |
| 6,514,750 B2 | 2/2003 | Bordenkircher et al. |
| 6,544,737 B1 | 4/2003 | Blumenfeld et al. |
| 6,551,836 B1 | 4/2003 | Chow et al. |
| 6,565,813 B1 | 5/2003 | Garyantes |
| 6,569,620 B1 | 5/2003 | Gold et al. |
| 6,572,828 B1 | 6/2003 | Potyrailo et al. |
| 6,576,478 B1 | 6/2003 | Wagner et al. |
| 6,579,358 B2 | 6/2003 | Delucas et al. |
| 6,579,367 B2 | 6/2003 | Vann et al. |
| 6,582,914 B1 | 6/2003 | Caldwell et al. |
| 6,602,702 B1 | 8/2003 | McDevitt et al. |
| 6,630,835 B2 | 10/2003 | Cheng et al. |
| 6,632,629 B2 | 10/2003 | Yang et al. |
| 6,638,761 B2 | 10/2003 | Shin et al. |
| 6,642,000 B1 | 11/2003 | Strizhkov et al. |
| 6,649,402 B2 | 11/2003 | Van der Weide et al. |
| 6,660,367 B1 | 12/2003 | Yang et al. |
| 6,664,044 B1 | 12/2003 | Sato |
| 6,677,151 B2 | 1/2004 | Sandell |
| 6,682,702 B2 | 1/2004 | Barth et al. |
| 6,689,323 B2 | 2/2004 | Fisher et al. |
| 6,703,236 B2 | 3/2004 | Atwood |
| 6,706,538 B1 | 3/2004 | Karg et al. |
| 6,713,309 B1 | 3/2004 | Anderson et al. |
| 6,716,629 B2 | 4/2004 | Hess et al. |
| 6,730,883 B2 | 5/2004 | Brown et al. |
| 6,737,026 B1 | 5/2004 | Bergh et al. |
| 6,743,633 B1 | 6/2004 | Hunter |
| 6,754,414 B2 | 6/2004 | Naghieh et al. |
| 6,783,732 B2 | 8/2004 | Madden et al. |
| 6,812,030 B2 | 11/2004 | Ozbal et al. |
| 6,821,486 B1 | 11/2004 | Akporiaye et al. |
| 6,827,831 B1 | 12/2004 | Chow et al. |
| 6,841,193 B1 | 1/2005 | Yang et al. |
| 6,841,663 B2 | 1/2005 | Lefkowitz et al. |

(56) References Cited

U.S. PATENT DOCUMENTS

| | | |
|---|---|---|
| 6,844,161 B2 | 1/2005 | Siani et al. |
| 6,848,462 B2 | 2/2005 | Covington et al. |
| 6,849,127 B2 | 2/2005 | Vann et al. |
| 6,858,185 B1 | 2/2005 | Kopf-Sill et al. |
| 6,861,035 B2 | 3/2005 | Pham et al. |
| 6,878,341 B2 | 4/2005 | Kowallis et al. |
| 6,878,554 B1 | 4/2005 | Schermer et al. |
| 6,893,877 B2 | 5/2005 | Hunter et al. |
| 7,133,726 B1 | 11/2006 | Atwood et al. |
| 7,159,740 B2 | 1/2007 | Nanthakumar et al. |
| 7,211,148 B2 | 5/2007 | Bryning et |
| 7,223,363 B2 | 5/2007 | McNeely et al. |
| 7,300,798 B2 | 11/2007 | Perbost et al. |
| 7,332,271 B2 | 2/2008 | O'Keefe et al. |
| 7,390,457 B2 | 6/2008 | Schembri |
| 7,459,130 B2 | 12/2008 | Pham et al. |
| 7,666,360 B2 | 2/2010 | Schellenberger et al. |
| 7,682,565 B2 | 3/2010 | Linton et al. |
| 7,842,246 B2 * | 11/2010 | Wohlstadter .......... B01L 3/5085 422/401 |
| 8,029,745 B2 * | 10/2011 | Hunter ................ B01F 13/0071 422/408 |
| 8,034,306 B1 | 10/2011 | Grudzien et al. |
| 8,222,048 B2 | 7/2012 | Fritchie et al. |
| 8,535,620 B2 | 9/2013 | Takagi |
| 2001/0046702 A1 | 11/2001 | Schembri |
| 2001/0053334 A1 | 12/2001 | Chen et al. |
| 2001/0055765 A1 | 12/2001 | O'Keefe et al. |
| 2002/0001544 A1 | 1/2002 | Hess et al. |
| 2002/0001546 A1 | 1/2002 | Hunter et al. |
| 2002/0003177 A1 | 1/2002 | O'Connor et al. |
| 2002/0005493 A1 | 1/2002 | Reese et al. |
| 2002/0015994 A1 | 2/2002 | Schellenberger et al. |
| 2002/0049196 A1 | 4/2002 | Carpino et al. |
| 2002/0072096 A1 | 6/2002 | O'Keefe et al. |
| 2002/0094533 A1 | 7/2002 | Hess et al. |
| 2002/0110900 A1 | 8/2002 | Jovanovich et al. |
| 2002/0119578 A1 | 8/2002 | Zaffaroni et al. |
| 2002/0151040 A1 | 10/2002 | O'Keefe et al. |
| 2002/0176804 A1 | 11/2002 | Strand et al. |
| 2002/0192716 A1 | 12/2002 | Schellenberger et al. |
| 2003/0003036 A1 | 1/2003 | Rouleau et al. |
| 2003/0039585 A1 | 2/2003 | Freeman |
| 2003/0064393 A1 | 4/2003 | Bass et al. |
| 2003/0064507 A1 | 4/2003 | Gallagher et al. |
| 2003/0080087 A1 | 5/2003 | Stelzle et al. |
| 2003/0108726 A1 | 6/2003 | Schembri et al. |
| 2003/0113726 A1 | 6/2003 | Tsuchihashi et al. |
| 2003/0119042 A1 | 6/2003 | Franco De Sarabia Rosado et al. |
| 2003/0124716 A1 | 7/2003 | Hess et al. |
| 2003/0124735 A1 | 7/2003 | Nanthakumar et al. |
| 2003/0138941 A1 | 7/2003 | Gong et al. |
| 2003/0165884 A1 | 9/2003 | Chow et al. |
| 2003/0170610 A1 | 9/2003 | Cima et al. |
| 2003/0180807 A1 | 9/2003 | Hess et al. |
| 2003/0186350 A1 | 10/2003 | Newell |
| 2003/0207099 A1 | 11/2003 | Gillmor et al. |
| 2003/0219716 A1 | 11/2003 | Avdeef et al. |
| 2003/0235521 A1 | 12/2003 | Shea et al. |
| 2004/0023223 A1 | 2/2004 | Thompson et al. |
| 2004/0033168 A1 | 2/2004 | Hughes et al. |
| 2004/0037748 A1 | 2/2004 | Hasan et al. |
| 2004/0109793 A1 | 6/2004 | McNeely et al. |
| 2004/0132040 A1 | 7/2004 | Hamill et al. |
| 2004/0141880 A1 | 7/2004 | Handler et al. |
| 2004/0171166 A1 | 9/2004 | Hunter |
| 2004/0191924 A1 | 9/2004 | Hunter et al. |
| 2004/0208792 A1 | 10/2004 | Linton et al. |
| 2004/0209303 A1 | 10/2004 | Martin |
| 2004/0235005 A1 | 11/2004 | Friedlander et al. |
| 2004/0241636 A1 | 12/2004 | Michnick et al. |
| 2005/0059074 A1 | 3/2005 | Schellenberger et al. |
| 2005/0079105 A1 | 4/2005 | Hunter et al. |
| 2005/0118073 A1 | 6/2005 | Facer et al. |
| 2005/0130213 A1 | 6/2005 | Morrison |
| 2005/0148066 A1 | 7/2005 | O'Keefe et al. |
| 2005/0214173 A1 | 9/2005 | Facer et al. |
| 2005/0220675 A1 | 10/2005 | Reed et al. |
| 2005/0266582 A1 | 12/2005 | Modlin et al. |
| 2006/0019410 A1 | 1/2006 | St. Claire |
| 2006/0057209 A1 | 3/2006 | Chapman et al. |
| 2006/0105433 A1 | 5/2006 | Bickmore et al. |
| 2006/0183171 A1 | 8/2006 | Schellenberger et al. |
| 2006/0194108 A1 | 8/2006 | Drews et al. |
| 2007/0117099 A1 | 5/2007 | Engelhardt et al. |
| 2008/0009071 A1 | 1/2008 | Sogard |
| 2008/0108112 A1 | 5/2008 | O'Keefe et al. |
| 2008/0293035 A1 | 11/2008 | Bergholtz et al. |
| 2009/0117620 A1 | 5/2009 | Fritchie et al. |
| 2011/0003699 A1 | 1/2011 | Yoder et al. |
| 2012/0122762 A1 | 5/2012 | Ruben et al. |
| 2012/0183968 A1 | 7/2012 | Lee et al. |
| 2013/0224877 A1 | 8/2013 | Phillips et al. |

FOREIGN PATENT DOCUMENTS

| | | |
|---|---|---|
| EP | 0402888 | 12/1990 |
| EP | 0506993 | 10/1992 |
| EP | 0236069 | 2/1997 |
| EP | 0882593 | 12/1998 |
| EP | 1155742 A2 | 11/2001 |
| JP | 63107057 | 5/1988 |
| JP | 02241539 | 9/1990 |
| JP | 09-281106 | 10/1997 |
| JP | 9281078 | 10/1997 |
| JP | 11061498 | 3/1999 |
| JP | 2000-028623 A | 1/2000 |
| JP | 2000-088863 A | 3/2000 |
| JP | 2000-287670 A | 10/2000 |
| JP | 200183163 | 3/2001 |
| JP | 2001-211873 A | 8/2001 |
| JP | 2001517936 | 10/2001 |
| JP | 2002-027984 A | 1/2002 |
| JP | 2002-189033 A | 7/2002 |
| JP | 2002283305 A | 10/2002 |
| JP | 2002335950 | 11/2002 |
| WO | WO-91/13335 | 9/1991 |
| WO | WO-95/01559 | 1/1995 |
| WO | WO-95/11755 | 5/1995 |
| WO | WO-97/00941 | 1/1997 |
| WO | WO-97/00943 | 1/1997 |
| WO | WO-97/15394 | 5/1997 |
| WO | WO-97/36167 | 10/1997 |
| WO | WO-97/37036 | 10/1997 |
| WO | WO-98/45406 | 10/1998 |
| WO | WO-98/47003 | 10/1998 |
| WO | WO-99/11373 | 3/1999 |
| WO | WO-99/19510 | 4/1999 |
| WO | WO-99/34920 | 7/1999 |
| WO | WO-99/39829 | 8/1999 |
| WO | WO-99/47922 | 9/1999 |
| WO | WO-99/52560 | 10/1999 |
| WO | WO-99/55461 | 11/1999 |
| WO | WO-9961152 | 12/1999 |
| WO | WO-0001798 | 1/2000 |
| WO | WO-00/56456 | 9/2000 |
| WO | WO-0051735 | 9/2000 |
| WO | WO-01/35079 | 5/2001 |
| WO | WO-01/38583 | 5/2001 |
| WO | WO-0161054 | 8/2001 |
| WO | WO-01/87335 | 11/2001 |
| WO | WO-01/92579 | 12/2001 |
| WO | WO-02/30561 | 4/2002 |
| WO | WO-0226394 | 4/2002 |
| WO | WO-0240158 | 5/2002 |
| WO | WO-02055199 | 7/2002 |
| WO | WO-02/083952 | 10/2002 |
| WO | WO-02078834 | 10/2002 |
| WO | WO-02/087764 | 11/2002 |
| WO | WO-02089982 | 11/2002 |
| WO | WO-03/002226 | 1/2003 |
| WO | WO-03/035229 | 5/2003 |
| WO | WO-03/035239 | 5/2003 |
| WO | WO-03/042697 | 5/2003 |

(56) References Cited

FOREIGN PATENT DOCUMENTS

| WO | WO-03/054488 | 7/2003 |
|---|---|---|
| WO | WO-2004/018104 | 3/2004 |
| WO | WO-2004074818 | 9/2004 |

OTHER PUBLICATIONS

Aldea, Carmen et al., "Rapid Deteetion of Herpes Simplex Virus DNA in Genital Uleers by Real-Time PCR Using SYBR Green I Dye as the Detection Signal", *Journal of Clinical Microbiology*, pp. 1060-1062.
Anonymous, "The Living Chip-Automated Microarray Technology for the Living Chip-Automated Microarray Technology for BioTrove, Inc. at", http://www.nist.gov.public.affairs/atp2000/00004362.htm, visited on Jun. 14, 2001, 2 pages.
Arndt, et al., "A Rapid Genetic Screening System for Identifying Gene-Specific Suppression Constructs for use in Human Cells,", *Nucleic Acids Research*, vol. 28, No. 6., pp. e15-i-viii (2000).
Ausubel, et al., "Current Protocols in Molecular Biology", iii-xii (1987).
Birren, et al., "Genome Analysis Laboratory Manual Series", *B. Birren, ed., Cold Spring Harbor Laboratory Press*, vols. 1-4, 1997-1999.
Borhnop, Darryl et al., "Biomedical nanotechnology Architectures and Applications", *4626 Proc. SPIE*, 2002, 560-69.
Brenan, Colin et al., A massively parallel microfluidics platform for storage and ultra high throughput screening, *Proc. SPIE*, 4626, 2002, 560-69.
Brown, J H. et al., "Charts for Counting Bacterial Colonies,", *37 Am. J. Public Heath Nations Health*, vol. 37, pp. 206-207 (1947).
Cadus, *Cadus Pharmaceutical Corp, 1997 Annual Report*, 1-29, May 8, 1998.
Coleman, et al., "Phospholipid Synthesis in Isolated Fat Cells,", *252 J. of Biological Chemistry*, vol. 252, pp. 3050-3056 (1977).
Cooper, Colin S. et al., "Applications of microarray technology in breast cancer research,", 3(3) *Breast Cancer Res.* 158-175 (2001).
De Macario, et al., *121 Methods in Ezymology 509-25* (1986).
De Macario, et al., "Adaption of the Slide Immuneozymatic Assay for Quantification of DNA Hybridization: SIA-DNA,", 8 *Biotechniques 210-217* (1990).
De Macario, et al., "Chemical Abstr.", abstract 67622t, 1985.
De Macario, et al., "Slide lmmunoenzymatic Assay for Human IgE(SIA-IgE),", *90 J. Immunological Methods 137-141* (1986).
Eckstein, et al., "Oligonucleotides and Analogues. A Practical Approach", *IRL Press,,* 1991.
Erfle, H et al., "Simultaneous loading of 200 sample lanes for DNA sequencing on vertical and horizontal, standard and ultrathin gels", vol. 25, No. 11 pp. 2229-2230, Oxford University Press, 1997.
Gait, "Oligonucleotide Synthesis—A Practical Approach", *IRL Press at Oxford University Press*, vii-xiii (1984).
Gillmor, S D. et al., "Low-Contact-Angle Polydimethyl Siloxane (PDMS) Membranes for Fabricating Micro-Bioarrays,", *Proc. 2d. Ann. Int'l IEEE-EMBS Spec Topic Conf. on Microtechnologies in Med. & Bio. 51* (A. Dittmar, ed. 2002).
Huhmer, Afr et al., "Noncontact Infrared-Mediated Thermocycling for Effective Polymerase Chain Reaction Amplification of DNA in Nanoliter Volumes,", *72 Anal Chem* 5507-5512 (2000).
Jones, T.B. et al., "Dielectrophoretic Liquid Actuation and Nanodroplet Formation", *J. Applied Phys.*, 99(2), 2001, 1441-42.
Kanigan, Tanya et al., "Living Chips for Drug Discovery,", *3926 Proc SPIE 172-180* (2000).
Kricka, L J. et al., "Microchip PCR", *377 Analytical and Bioanalytical Chemistry*, 377, pp. 820-825 (2003), 2003, 820-825.
Lee, Da-Sheeng et al., "A novel real-time PCR machine with a miniature spectrometer for fluorescence sensing in a micro liter volue glass capillary", *100 Sensors and Actuators B 401-10*, 2004.
Lennon, Gregory , ""High-throughout gene expression analysis for drug discovery"", *Drug Discovery Today*, 5(2), 2000, 59-66.

Limbach, Patrick et al., "Advances in Nucleic Acid and Protein Analyses, Manipulation, and Sequencing", *Proc. SPIE*, 2000, 171-180.
MacBeath, G. et al., "Printing Proteins as Microarrays for High-Throughput Function Determination", *Science* 289, Sep. 2000, 1760-1763.
Maniatis, et al., "Molecular cloning: a laboratory manual", Cold Spring Harbor Laboratory, 1982, v-x.
Marras, S. E. et al., "Multiplex detection of single nucleotide variations using molecular beacons", *Genet. Anal.: Biomol. Eng,.* 14:, Elsevier Science B.V., 1999, 151-156.
Matsubara, Y et al., "Microchamber Array Based DNA Quantification and Specific Sequence Detection from a Single Copy Via PCR in Nanoliter Volumes", *20 Biosensors and Bioelectronics 1482-1490* (2005).
Matsubara, Y et al., "On-chip Nanoliter-Volume Multiplex Taqman Polymerase Chain Reaction From a Single Copy Based on Counting Fluorescence Released from Microchambers,", *21 Anal Chem.* 6434-6439 (2004).
McGraw-Hill, "Dictionary of Scientific & Technical Terms 2151", 6th Ed., 2003.
Moerman, R et al., "Miniaturized Electrospraying as a Technic for the Production of Microarrays of Reproducible Micrometer Sized Protein Spots, in Micro Total Analysis Systems 2000: Proceedings of the u TAS 2000 Symposium", May 14-18, 2000.
Morris, Timothy et al., "Rapid Reverse Transcription-PCR Detection of Hepatitis C Virus RNA in Serum by Using the TaqMan Fluorogenic Detection System", *Journal of Cunical Microbiology*,34(12), Dec. 1996, 2933-2936.
Nagai, H et al., "Development of a Microchamber Array for Picoliter PCR", *73 Anal. Chemistry 1043-1047* (2001).
Nagai, H et al., "High-Throughput PCR in Silicon Based Microchamber Array,", *16 Biosensors & Bioelectronics 1015-1019* (2001).
Patrick Adlecreutz & Bo Mattiass, Oxygen Supply to Immobilized Cells, *16 Eur. J. Appl. Biotechnology 165-170* (1982).
PCT/US06/36299, "International Preliminary Report on Patentability mailed Mar. 18, 2008".
PCT/US06/36299, "International Search Report mailed Jun. 8, 2007".
PCT/US06/36299, "Written Opinion of the International Searching Authority mailed May 4, 2007".
Polokoff, et al., "Isolation of Somatic Cell Mutants Defective in the Biosynthesis of Phoshatidylethanolamine", *256 J. Biological Chemistry*, pp. 7687-7690 (1981).
Prescott, et al., "Microbiology", *Wm. C. Brown Publishers*, 1990, pp. 31; 114-116.
Rolls, et al., "A Visual Screen of GFP-Fusion Library Identifies a New Type of Nuclear Envelope Membrane Protein,", *J. Cell Biol.*, vol. 146, No. 1, pp. 29-43 (1999).
Sambrook, et al., "Ch: 6.6-6.13", *Molecular Cloning: A Laboratory Manual, Second Edition*, vol. 1,, 1989, 6.6-6.13.
Sauter, A D. "Nanoliters onto media: Use of Electric Induction,", *American Laboratory 40-45* (Oct. 2001).
Shoffner, Mann A. et al., "Chip PCR. I. Surface passivation of microfabricated silicon-glass chips for PCR,", 24(2) *Nucleic Acids Research* 375-379 (1996).
Sieweke, "Direction of Transcription Factor Partners with a Yeast One Hybrid Screen,", *Methods of Mol. Biol.*, vol. 130, pp. 59-77 (2000).
Singh-Gasson, et al., "Maskless fabrication of light-directed oligonucleotide microarrays using a digital Micromirror array", *Nature Biotechnology*, vol. 17, 1999, 974-978.
Smith, et al., "Dynamical Scaling of DNA Diffusion Coefficients", vol. 29, pp. 1372-1373, *Macromolecules*, 1996.
Sosnowski, Manufacturing Methods for High Density Micro-Channel Arrays, (Master's Thesis) Massachusetts Institute of Technology Dep't of Mechanical Engineering, 2000.

(56) References Cited

OTHER PUBLICATIONS

Steel, Adam et al., "The Flow-Thru Chip: A Three Dimensional Biochip Platform, in Microarray Biochip Technology", 87-117 (*Mark Schena ed.* 2000).

Taylor, Theresa B. et al., "Optimization of the Performance of the Polyermase Chain Reaction in Silicon-Based Microstructures", vol. 25, No. 15 *Nucleic Acids Research* pp. 3164-3168 (1997), Jun. 22, 1997.

The American Heritage College Dictionary 1416, *3rd Ed.*, 2000.

Thorstenson, et al., "Global Analysis of ATM Polymorphism Reveals Significant functional Constraint", *American Journal of Human Genetics*, 69:396-412.

Tian-Lu Cheng, et al., ""Membrane-Tethered Proteins for Basic Research, Imaging and Therapy"", *Medical Research Reviews*, May 14, 2008.

Vogelstein, et al., "Digital PCR", *Proc. Natl. Acad. Sci. USA*, vol. 96, Aug. 1999, 9236-9241.

Vykoukal, J. et al., "A Programmable Dielectrophoretic Fluid Processor for Droplet-Based Chemistry", *Micro Total Analysis Systems*, 2001, 72-74.

Weast, PHD, Robert C., "CRC Handbook of Chemistry and Physics, Ed.", *65th Edition* pp. F-20-F35, 1984-1985.

Wittwer, C. T. et al., "Continous Fluorescence Monitoring of Rapid Cycle DNA Amplification", *Biotechniques, Informa Life Sciences Publishing*, Westborough, MA, vol. 22, No. 1, Jan. 1, 1997, 130-138.

Wittwer, C.T. et al., "The LightCycler™: A Microvolume Multisample Fluorimeter with Rapid Temperature Control", *BioTechniques*, vol. 22 (1), Jan. 1997, 176-181.

Zhao, et al., "Directed Evolution Converts Subtilisin E into a Functional Equivalent of Thermitase,", *Protein Eng.*, vol. 12. No. 1, 47-53 (1999).

Zubritsky, Elizabeth, "Spotting a microarray system", *Modern Drug Discovery*, 4(5), 2001.

\* cited by examiner

User Removes Excess Sample

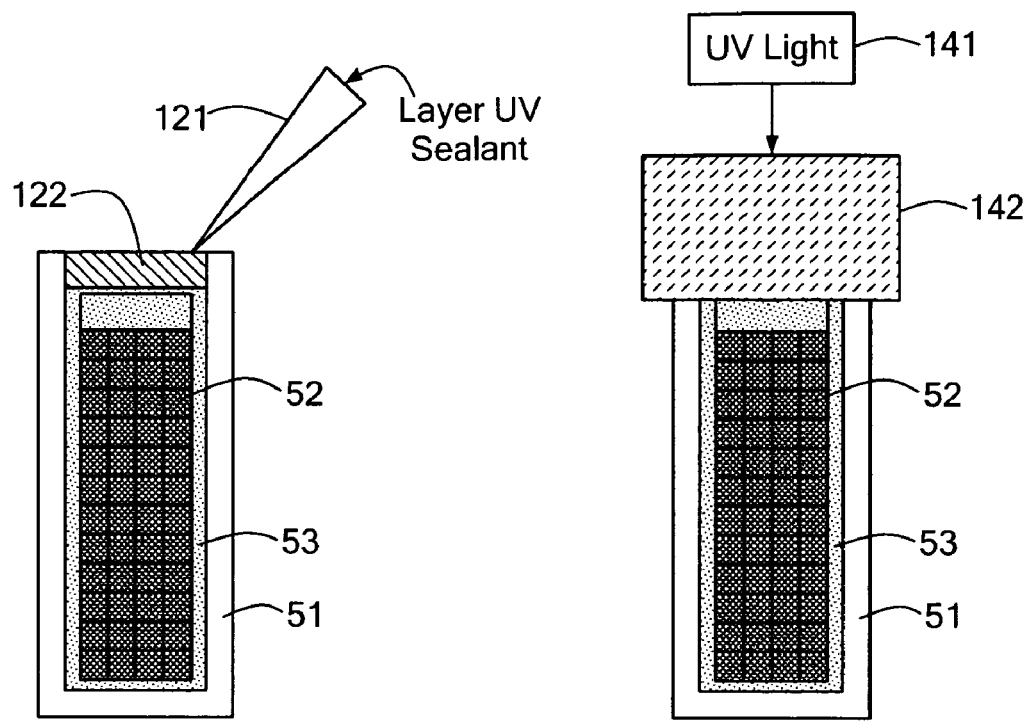
FIG. 13          FIG. 14
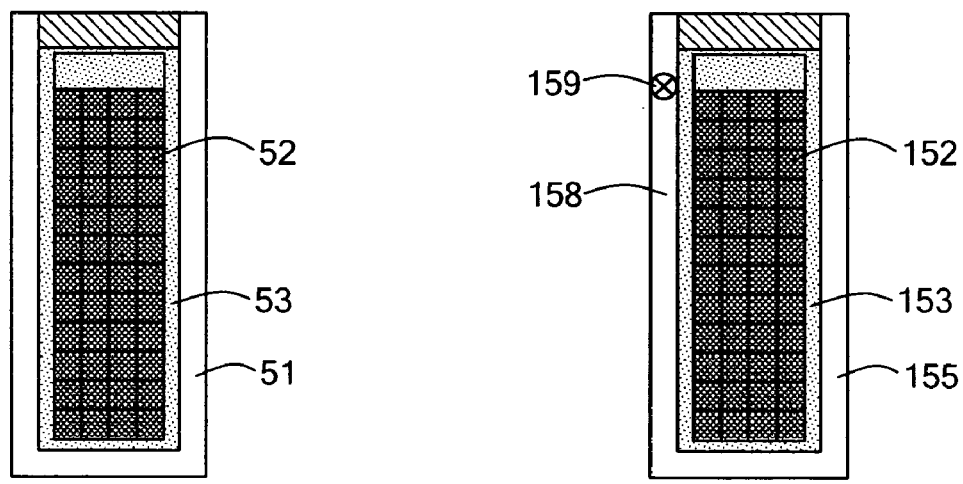
FIG. 15(a)          FIG. 15(b)

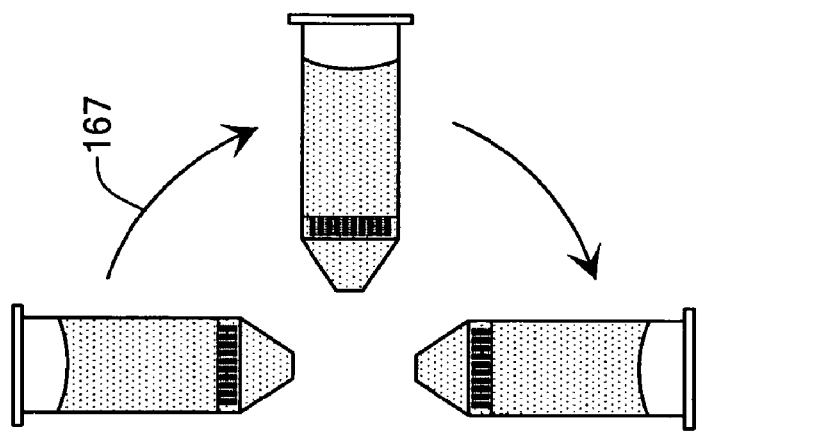
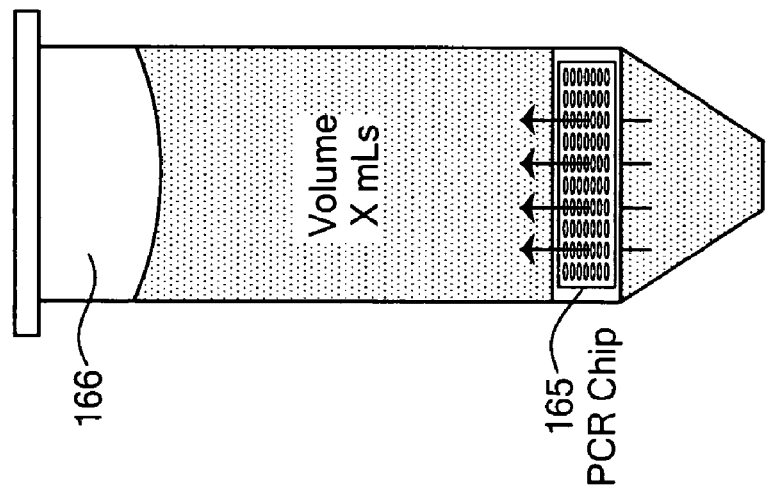
FIG. 16(b)
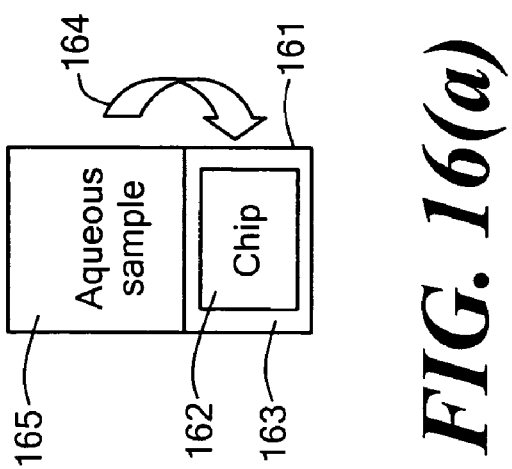
FIG. 16(a)

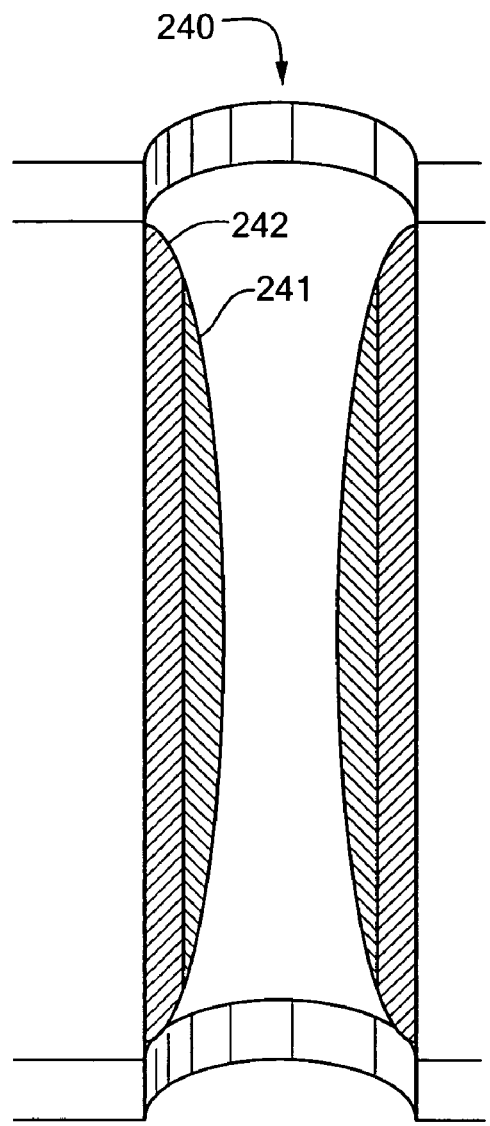 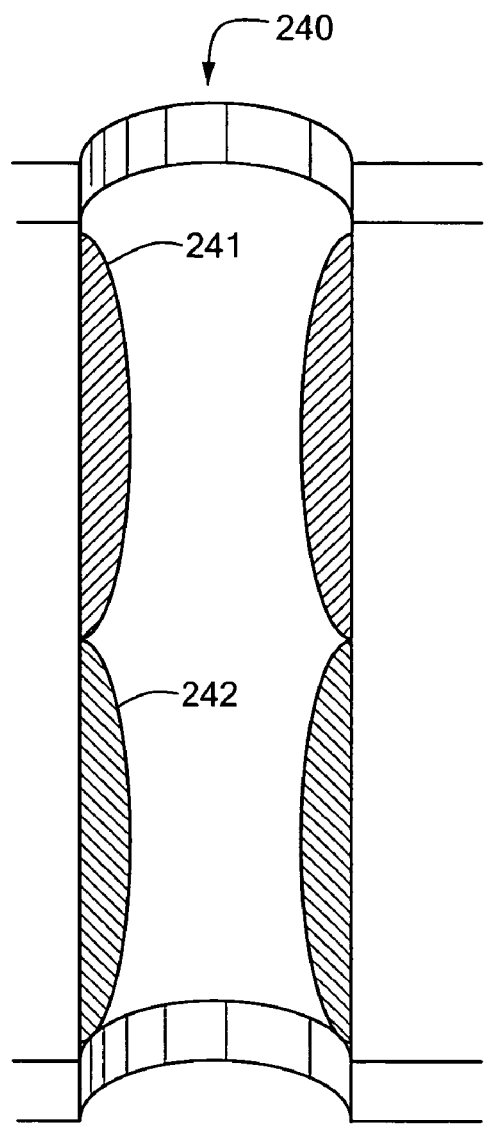
*FIG. 24(a)*   *FIG. 24(b)*

THERMAL CYCLING APPARATUS AND METHOD

CROSS REFERENCE TO RELATED APPLICATIONS

This application is a continuation application of U.S. patent application Ser. No. 13/491,989, filed on Jun. 8, 2012, which is a continuation application of U.S. patent application Ser. No. 12/243,503, filed on Oct. 1, 2008, which is a divisional application of U.S. patent application Ser. No. 10/744,580, filed on Dec. 22, 2003, now U.S. Pat. No. 7,682,565, which claims priority from U.S. provisional patent application No. 60/434,988, filed Dec. 20, 2002, U.S. provisional patent application No. 60/461,559, filed Apr. 9, 2003, U.S. provisional patent application No. 60/528,461, filed Dec. 10, 2003, and U.S. provisional patent application No. 60/461,556, filed Apr. 9, 2003. Each of these patent applications described in this paragraph is hereby incorporated by reference, in its entirety.

FIELD OF THE INVENTION

The present invention relates to devices and methods for assaying samples in nanoliter volumes, potentially for achieving high throughput screening and for other purposes where the ability to assay low-volume samples at high densities is desired.

BACKGROUND ART

Rapid, sensitive, specific, and cost-effective biochemical assays are needed for a variety purposes. For example, the recent emergence of Sudden Acute Respiratory Syndrome (SARS) and national security bio-threats indicate the need to identify infectious agents or toxins for appropriate therapeutic intervention. It would be valuable to be able to simultaneously detect and identify in clinical samples a broad range of infectious agents such as the corona virus responsible for SARS. Another example is the need for more sensitive, specific, accurate, reliable, easy to use, and inexpensive research tools to measure RNA expression patterns of small cell numbers, such as might be obtained from a laser-capture microdissection.

One primary challenge for bio-defense and diagnostic applications is the early detection of infections, which typically requires increasing assay sensitivity. Presently, the most sensitive and widely used molecular diagnostic methods are based on real-time Polymerase Chain Reaction (PCR) methods such as TaqMan® for amplifying pathogen-nucleic acids. However, these methods suffer from several limitations:

1) The cost of the assays and amount of sample needed are often too prohibitive to run large numbers of assays against a patient sample.

2) The assays amplify but do not concentrate nucleic acids. For example, if there are 10 copies of SARS RNA in a patient sample, performing assays against 20 viral sequences involves a significant risk of obtaining a false negative test result.

3) Multiplexing numerous assays is quite difficult due to the need to harmonize reaction conditions and separate results into different optical channels. A typical problem in PCR multiplexing is the competition between the many primers.

4) Screening for potential bio-terrorism agents tend to be done only at the state and federal level, and not at the clinic or local level. That is because even with an assay that was 99.9% accurate, the numerous false positives that would occur with widespread screening would result in unreasonable expense as well as economic and political disruption. Thus, there is a need for a great increase in the reliability of such tests.

Some of these problems can be addressed by using parallel microfluidic assay arrays. One example of such an array is the Living Chip™ marketed by Biotrove, Inc. of Woburn, Mass. In function and purpose, the Living Chip™ is similar to 96- and 384-well microtiter plates currently used in high-throughput screening and diagnostics. However, the approximately 35 nl sample volume held by each sample well in the Living Chip™ is roughly 2000 times less than that in a 96-well plate, and 200 times less than a 384-well plate.

FIG. 1 shows a cut away view of a typical microfluidic sample array of through-holes. Such an array is described, for example, in U.S. Pat. No. 6,387,331 and U.S. Patent Application 20020094533, the contents of which are incorporated herein by reference. The sample array 10 includes a sheet of material 14 having a pair of opposed surfaces and a thickness. The sheet of material 14 may be a platen, otherwise referred to herein as a chip, and may made of, for example, conductive silicon, or other types of rigid materials, such as metal, glass, or plastic. A large number of through-holes 12 run through the thickness from one of the surfaces 14 to the other opposing surface (not shown).

The sample array 10 typically may be from 0.1 mm to more than 10 mm thick; for example, around 0.3 to 1.52 mm thick, and commonly 0.5 mm. Typical volumes of the through-holes 12 may be from 0.1 picoliter to 1 microliter, with common volumes in the range of 0.2-100 nanoliters, for example, about 35 nanoliters. Capillary action or surface tension of the liquid samples may be used to load the sample through-holes 12. For typical chip dimensions, capillary forces are strong enough to hold liquids in place. Chips loaded with sample solutions can be waved around in the air, and even centrifuged at moderate speeds without displacing samples.

To enhance the drawing power of the through-holes 12, the target area of the receptacle, interior walls 13, may have a hydrophilic surface that attracts a liquid sample. It is often desirable that the surfaces be bio-compatible and not irreversibly bind biomolecules such as proteins and nucleic acids, although binding may be useful for some processes such as purification and/or archiving of samples. Alternatively, the sample through-holes 12 may contain a porous hydrophilic material that attracts a liquid sample. To prevent cross-contamination (crosstalk), the exterior planar surfaces 14 of chip 10 and a layer of material 15 around the openings of sample through-holes 12 may be of a hydrophobic material. Thus, each through-hole 12 has an interior hydrophilic region bounded at either end by a hydrophobic region.

The use of through-holes 12, as compared to closed-end well structures, reduces the problem of trapped air inherent in other microplate structures. The use of through-holes together with hydrophobic and hydrophilic patterning enables self-metered loading of the sample through-holes 12. The self-loading functionality helps in the manufacture of arrays with pre-loaded reagents, and also in that the arrays will fill themselves when contacted with an aqueous sample material.

It has been suggested that such arrays can be utilized for massively parallel PCR analysis of a given sample. For example, International Patent Application WO 01/61054 (incorporated herein by reference) suggests that sample probes and PCR reagents can be dried onto the walls of the sample wells. One problem that has been observed with this approach is that when the array is immersed in a sample liquid to load the through-holes, the dried probes and reagents can dissolve and float away out of the sample wells that they were loaded in.

Additionally, with PCR, a series of heating and cooling cycles is used to replicate a small amount of DNA into a much larger amount. Thermal cyclers are devices that generate such a series of heating and cooling cycles. Current thermal cycling approaches are not well suited for thermal cycling of sample arrays such as the one shown in FIG. 1. Unlike standard microtiter plates having closed-end storage wells, the sample arrays with through-holes cannot be simply set on a temperature controlled thermal block because some or all of the samples can be wicked out of their storage channels onto the supporting plate. Nor are such through-holes suitable for immersion in a temperature controlled circulating fluid because the fluid would be free to enter the hole openings and could mix with or extract the contents of the through-holes. Also, if fluid flow is used to produce a temperature change, pressure differences within the fluid can cause the sample to leave the through-holes.

The great densities and small volumes for the through-holes 12 of the sample array pose further challenges to implementing various complex assays in such systems. Such challenges include risks of (i) chemical and physical interactions between adjacent through-holes, (ii) loss of sample below an amount permitting reliable assay, (iii) non-uniformity of assay from through-hole to through-hole, so as to impair the reliability of assays using such systems, (iv) the ability to load samples into the array, and (v) inhibitory or otherwise unfavorable interactions between the surfaces of the array and the reagents or samples in the reactions.

SUMMARY OF THE INVENTION

In a first embodiment of the invention there is provided a system for holding at least one of sample and reagent for analysis. The system includes a pair of parallel covers. At least one of the pair of parallel covers is light transmissive, of which pair a light transmissive cover forms a top, and of which pair the other forms a bottom. A frame is disposed between the covers to define, in relation to the covers, an interior volume. The frame and the covers are associated with one another to form a case that is substantially tight to liquids. A microfluidic array is disposed in the interior volume. The array includes a sheet of material having a pair of opposed surfaces, a thickness, and a plurality of through-holes running through the thickness between the surfaces. The through-holes contain at least one of sample and reagent.

In accordance with another embodiment of the invention, a system for holding at least one of sample and reagent for analysis is presented. The system includes a pair of parallel covers, at least one of which is light transmissive, and of which pair a light transmissive cover forms a top, and of which pair the other forms a bottom. A frame is disposed between the covers to define, in relation to the covers, an interior volume. The frame and the covers are associated with one another to form a case. The case includes a sealable opening, which when sealed renders the case substantially tight to liquids. A microfluidic array is disposed in the interior volume and is removable via the opening. The array includes a sheet of material having a pair of opposed surfaces, a thickness, and a plurality of through-holes running through the thickness between the surfaces. The through-holes containing at least one of sample and reagent.

In accordance with still another embodiment of the invention, a method of conducting an assay on a plurality of samples is presented. A microfluidic array is provided. The array includes a sheet of material having a pair of opposed surfaces, a thickness, and a plurality of through-holes running through the thickness between the surfaces. Each of the through-holes contains one of the samples and at least one reagent providing an optical effect for assay purposes. The array is place in a case that is substantially tight to liquids. The case includes a pair of parallel covers, at least one of which is light transmissive, and of which pair a light transmissive cover forms a top, and of which pair the other forms a bottom. A frame is disposed between the covers to define, in relation to the covers, an interior volume for receiving the array. The corresponding sample in each of the through-holes is permitted to react with the at least one reagent therein. A measurement is obtained, through the top cover, for each through-hole, of the optical effect associated therewith and the measurement is used to provide assay results for the corresponding sample therein.

In various embodiments related to the invention as described herein, a spacer means is provided for ensuring space between at least one of the covers of the case and at least a portion of the array. The top-cover and the spacer means may be dimensioned to provide a distance of less than 0.5 mm from an upper surface of the top cover to a proximate surface of the array. The spacer means may include a plurality of beads or posts affixed to one of (i) the array and (ii) at least one of the covers, and/or an increase in thickness of the array over a defined set of locations thereof. One or more positioning guide rails may be affixed to at least one of (i) the frame and ii) at least one of the covers. The array may include a recess at an opening of each through-holes, the recess preventing fluid in each through-hole from coming into contact with a cover to which each such through-hole is proximate. The dimensions of the case may be approximately 25×76×<2 mm, such that the case has the approximate size and shape of a microscope slide. The frame of the case may includes walls defining a hole, the hole filled with a self-sealing material, such as grease, and the frame may be a gasket that can be penetrated by a syringe. The frame and the covers may be coupled together to form the case by an epoxy or other adhesive. In various embodiments, the frame may be, or include, an adhesive gasket, and/or a compression gasket.

In further related embodiments to the invention described herein, a funnel guide may be coupled to the case, the array capable of being inserted into the case by passing the array through the funnel guide and an opening of the case. The funnel guide may be removably attached to the case. The funnel guide may include walls defining a slit, the array capable of being passed through the slit. Liquid may be substantially prevented from passing through the slit in the absence of the array due to, for example, surface energy. The walls defining the slit may be capable of being deformed to allow the array to pass through the slit, and may be made, for example, of plastic. The slit may be capable of being opened and closed. The funnel guide may include brushes for spreading of the at least one of sample and reagent. The at least one cover of which is light transmissive may be coated with a hydrophilic layer to prevent fogging. At least one of the frame and the covers may includes a hydrophilic strip for promoting spreading of sample during array loading. At least one of the array and the case may include an identifier, such as a barcode.

Another embodiment of the present invention includes a thermal cycling device and corresponding method. A fluid delivery system develops a flow of controlled-temperature fluid, which may be selectable between a first controlled temperature and at least a second controlled temperature. A sample plate cartridge has a cavity for holding a high-density microfluidic sample plate. A cycling head holds the sample plate cartridge and delivers the flow of fluid over the sample plate cartridge.

A further embodiment may include a thermal sensor for sensing temperature of the flow of fluid. The sample plate cartridge may also include at least one transparent cover over the sample plate, and the cycling head may include at least one transparent window arranged for imaging of samples in the sample plate. A Peltier device may be associated with the cycling head for controlling temperature of the fluid.

The cycling head may be adapted for vertical orientation of the sample plate cartridge. The sample plate cartridge may include a guide rail arrangement for holding the sample plate, and/or may be capable of holding a plurality of sample plates. Alternatively or in addition, the cycling head may include a guide rail arrangement for holding the sample plate cartridge.

The sample plate cartridge or the cycling head may be adapted to deliver a laminar flow of fluid over the sample plate cartridge. The cycling head may include a flow regulator for promoting uniform flow of fluid over the sample plate cartridge. The flow regulator may include a flow restrictor or flow inlet cavity in the cycling head upstream of the sample plate cartridge. A volume of fluid that is immiscible with the sample such as (for aqueous samples) a perfluorinated hydrocarbon liquid may be provided in the sample plate cartridge cavity for covering an inserted sample plate.

In an embodiment, the sample plate may have a top surface and a bottom surface which are connected by a plurality of through-holes, and the sample plate cartridge may have an associated top cover and bottom cover. In such an embodiment, the sample plate cartridge and the cycling head may be adapted so that the flow of fluid is delivered over both the top cover and the bottom cover.

Another embodiment of the present invention is directed to a microfluidic array which includes a platen having a high-density microfluidic array of through-holes. A biocompatible and/or hydrophilic coating is coupled to walls of at least one through-hole well of the array. Encapsulated in the coating is a primer for amplifying a nucleotide sequence of a sample introduced into the through-hole. The coating may be covalently bonded or dried to the interior walls of the through-holes. The biocompatible material may be a polymer such as polyethylene glycol. The primer may be for PCR assaying. A second layer of polymer may be added to the top of the coating. In various embodiments, the array may include a layer of hydrophobic material around the opening of each through-hole, so as to isolate each through-hole from other through-holes. The platen may be arranged for stacking with another platen to promote a desired chemical reaction in each through-hole.

In various embodiments, a sample containing nucleic acid can be introduced to a sample platen that includes an array having capture probes, so as to form a hybridized array of samples. Then, PCR sequencing can be performed on the hybridized array. In some embodiments, this may involve providing a second reagent platen having a high-density microfluidic array of through-holes, in which each through-hole contains a volume of PCR reagent, and in which the reagent platen has a structural geometry that corresponds to the sample platen. Then, one platen can be stacked on top of the other so as to deliver PCR reagent to samples in the hybridized array. In various embodiments, the hybridized array may be washed, prior to stacking, with a buffer to remove on-specifically bound nucleic acids.

Another representative embodiment of the present invention includes a microfluidic array for thermal cycling. A platen has a layer of hydrophobic material surrounding the openings of through-holes of the array that include a biocompatible and/or hydrophilic coating, wherein at least one through-hole includes a covalently or non-covalently immobilized nucleic acid component for assaying. The nucleic acid component may be immobilized in a hydrophilic polymer and/or a melting polymer that melts during assaying so as to release the nucleic acid component into solution in the at least one through-hole. For example, the polymer may be based on polyethylene glycol (PEG). The nucleic acid component may be a primer or a probe for polymerase chain reaction (PCR) assaying.

A corresponding method of biochemical assaying starts by loading a polymer solution containing a nucleic acid into at least one through-hole in an high-density microfluidic array of through-holes, the array having a layer of hydrophobic material surroundings the openings of the through-holes, and each through-hole containing a hydrophilic material. The solution is then dried so that a nucleic acid component is immobilized within the at least one through-hole.

The method may further include loading a nucleic acid target component into the at least one through-hole, and then thermal cycling the array and performing a PCR assay. The loading may be based on dipping the array into a solution containing the nucleic acid target component, and then withdrawing the array from the solution. Alternatively, the nucleic acid target component may be pippetted into the at least one through-hole, or a drop of solution containing the nucleic acid target component may be moved relative to the opening of the at least one through-hole. The thermal cycling may include developing a flow of controlled-temperature fluid; loading the array into a sample plate cartridge having a cavity for holding a high-density microfluidic sample plate; and delivering the flow of controlled-temperature fluid over the sample plate cartridge.

In accordance with another embodiment of the invention, a biochemical assay structure and method includes a chip having a microfluidic array of through-holes. The through-holes are adapted for: capture of one or more targets of interest from a liquid sample introduced into the individual through-hole; and chemical processing of the captured one or more targets.

In related embodiments of the invention, the target capture may be based on a capture structure immobilized within the individual throughholes, such as a nucleic acid probe. The capture structure may be a protein, an antibody, and/or an aptamer. The capture structure may be covalently immobilized. The capture structure may be selected from antibodies, proteins, peptides, peptide nucleic acids, and oligonucleotides. The chemical processing may include amplification of the captured one or more targets. The amplification may include at least one of polymerase chain reaction (PCR) amplification and reverse transcription. The chemical processing may include detection of a signal from the captured one or more targets. The chemical processing may be specific to the captured one or more targets. The structure may be adapted to perform lysis of a target pathogen, or to perform ELISA analysis. The individual through-holes may include a layer of wax containing at least one reagent for the target capture or chemical processing. The wax may include polyethylene glycol (PEG), and/or have a melting point above 40° C. The individual through-holes may include a plurality of layers of wax, at least one of the layers containing the at least one reagent. Each layer of wax may have a different melting point and/or a different reagent. The surfaces of the through-holes may be biocompatible to avoid binding bio-molecules.

In further related embodiments of the invention, the assay structure and/or method may further include a first chip layer having a microfluidic array of through-holes and a second chip layer having a microfluidic array of through-holes. The first chip layer and the second chip layer are fixedly coupled such that the through-holes of each are aligned. The individually aligned through-holes may be, for example, adapted for the target capture and the chemical processing. The first and second chip layers may be coupled by an adhesive, screws, bolts, rivets, and/or clamps.

In accordance with another embodiment of the invention, a method of conducting an assay on a plurality of samples includes performing an assay at each sample site in a sample array having greater than 100 sample sites. Each assay provides an optical effect. Each of the sample sites simultaneously imaged to produce imaging data pertinent to the optical effect of each site.

In related embodiments of the invention, the sample array has greater than 500 sample sites, or greater than 1600 sample sites. Performing the assay may include performing replication cycles by Polymerase Chain Reaction (PCR). Imaging may include simultaneously imaging each sample site during each replication cycle. Each sample site may be simultaneously illuminated using one or more LEDs. The method may further include analyzing the imaging data.

In accordance with another embodiment of the invention, a method of conducting an assay on a plurality of samples includes performing an assay at each of a plurality of sample sites in a sample array, the sample array having a sample site density greater than one sample site per 20 mm². Each assay provides an optical effect. Each of the sample sites is simultaneously imaged to produce imaging data pertinent to the optical effect of each site.

In related embodiments of the invention, performing the assay includes performing replication cycles by Polymerase Chain Reaction (PCR). Imaging may include simultaneously imaging each sample site during each replication cycle. Each sample site may be simultaneously illuminated using one or more LEDs. The method may further include analyzing the imaging data.

In accordance with another embodiment of the invention, a method of conducting an assay on a plurality of samples includes performing an assay at each of a plurality of sample sites in a sample array. Each assay provides an optical effect. Each sample site is simultaneously illuminated using one or more colored LEDs. Furthermore, each of the sample sites is simultaneously imaged to produce imaging data pertinent to the optical effect of each site.

In related embodiments of the invention, performing the assay may include performing replication cycles by Polymerase Chain Reaction (PCR). Each sample site may be simultaneously imaged during each replication cycle. The method may further include. analyzing the imaging data.

In accordance with another embodiment of the invention, a system for conducting an assay on a plurality of samples includes a case having a fluid-tight cavity defining an interior volume. A microfluidic array is disposed in the interior volume, the array including a sheet of material having a pair of opposed surfaces, a thickness, and a plurality of through-holes running through the thickness between the surfaces. A thermal cycler is adapted to thermally contact the case In related embodiments of the invention, the thermal cycler may be a flat block having at least one thermally controlled surface. The flat block may be a Peltier device. A heat transfer pad may be positioned between the case and the surface. The thermal cycler may include a fluid delivery module for delivering a flow of controlled-temperature fluid over the case. The system may include an illumination source capable of illuminating each of the through-holes simultaneously. The illumination source may include at least one color LCD. The at least one LCD may be filtered by an excitation filter. A camera may simultaneously image each of the through-holes to provide imaging data. The system may further include a processor for processing the imaging data. The case may include a pair of parallel covers, at least one of which is light transmissive, of which pair a light transmissive cover forms a top, and of which pair the other forms a bottom. A frame disposed between the covers defines, in relation to the covers, an interior volume, the frame and the covers associated with one another to form the case. An encapsulation fluid, which reduces interactions between contents of distinct through-holes, may be disposed in the interior volume.

In accordance with another embodiment of the invention, a system includes a case having a fluid-tight cavity defining an interior volume. A microfluidic array is disposed in the interior volume, the array including a sheet of material having a pair of opposed surfaces, a thickness, and a plurality of through-holes running through the thickness between the surfaces. The system further includes an illumination source for simultaneously illuminating each of the through-holes, and a camera for simultaneously imaging each of the through-holes to produce imaging data.

In related embodiments of the invention, the illumination source includes at least one Light Emitting Diode (LED). The at least one LED may be a colored LED. An excitation filter may filter the at least one LED. At least one LED may be symmetrically positioned off-axis from the camera with reference to the array. The camera may be one of a Charge-Coupled Device (CCD) or Complimentary Metal-oxide Semiconductor (CMOS) camera. The system may include an emission filter for filtering light entering the camera. The array may have greater than 100 through-holes, greater than 500 through-holes, or greater than 1600 through-holes. The array may have a through-hole density greater than one through-hole per 20 mm², or greater than one sample sites per 0.25 mm². In various embodiments, the system may further include a processor for analyzing the imaging data.

In accordance with another embodiment of the invention, a system for holding at least one of sample and reagent for analysis includes a pair of parallel covers, at least one of which is light transmissive, of which pair a light transmissive cover forms a top, and of which pair the other forms a bottom. A frame is disposed between the covers to define, in relation to the covers, an interior volume, the frame and the covers associated with one another to form a case. The case has a sealable opening, such opening when sealed rendering the case substantially tight to liquids. A microfluidic array is disposed in the interior volume and removable via the opening. The array includes a sheet of material having a plurality of sample sites, the sample sites containing at least one of sample and reagent.

In related embodiments of the invention, the array may include a hydrophobic surface surrounding the openings of each sample site. The sample sites may include a hydrophilic surface that attracts the at least one of sample and reagent. The sheet may have a pair of opposed surfaces and a thickness, and the sample sites include a plurality of through-holes running through the thickness between the surfaces. The sample sites may include a plurality of closed-ended wells. At least one cover of which is light transmissive may be coated with a hydrophobic layer to prevent fogging. The array may include a recessed opening at each sample site, the recess preventing fluid in each sample site from coming into contact with a cover to which each such sample site is proximate. The system may further include one of a UV curable sealant and a grease for sealing the opening. The frame and the covers may be coupled together to form the case by at least one of an epoxy or other adhesive. The frame may be, or include, an adhesive gasket or a compression gasket. The frame may be puncturable and include includes walls defining a hole, the hole filled with a self-sealing material, which may be, for example, a grease. The system may further include a funnel guide coupled to the case, the array capable of being inserted into the case by passing the array through the funnel guide and the opening. The funnel guide may be removably attached to the case. The funnel guide may includes walls defining a slit, the array capable of being passed through the slit. Liquid may be substantially prevented from passing through the slit in the absence of the array due to, at least in part, surface energy. The walls defining the slit may be capable of being deformed to allow the array to pass through the slit. The funnel guide may include brushes for spreading of the at least one of sample and reagent. At least one of the frame and the covers may include a hydrophilic strip for promoting spreading of sample during array loading.

BRIEF DESCRIPTION OF THE DRAWINGS

The foregoing features of the invention will be more readily understood by reference to the following detailed description, taken with reference to the accompanying drawings, in which:

FIGS. 5 through 16 are diagrams illustrating an embodiment by which a user may perform assays using the system described in connection with FIG. 2;

FIG. 5 and FIG. 6 are diagrams illustrating the addition of encapsulation fluid to a case, in accordance with an embodiment of the present invention;

FIG. 7 and FIG. 8 are diagrams illustrating the addition of sample to the case of FIG. 6, in accordance with an embodiment of the present invention;

FIGS. 9 and 10 are diagrams illustrating the insertion of a microfluidic array into the case of FIG. 8, in accordance with an embodiment of the present invention;

FIG. 11 is a diagram illustrating the removal of excess sample from the case of FIG. 10, in accordance with an embodiment of the present invention;

FIGS. 12 and 13 are diagrams illustrating the application of a sealant to the case of FIG. 11, in accordance with an embodiment of the present invention;

FIG. 14 is a diagram illustrating the use of ultraviolet light to cure the sealant applied in the manner illustrated in FIG. 13, in accordance with an embodiment of the present invention;

FIG. 15(a) is a diagram illustrating a sealed case resulting from practice of the method of FIG. 14, in accordance with an embodiment of the present invention;

FIG. 15(b) is a diagram illustrating a top view of a sealed case that includes a grease lock, in accordance with an embodiment of the present invention;

FIG. 16(a) is a diagram illustrating the introduction of a sample into through-holes of a microfluidic array in accordance with an embodiment of the present invention in which turbulence is introduced into the case;

FIG. 16(b) is a diagram illustrating the introduction of a sample into through-holes of a nano-liter array in accordance with an embodiment of the present invention, in which the microfluidic array is rotated;

FIG. 24(a-b) is a diagram illustrating a through-hole of a microfluidic array that includes layers of various material, in accordance with an embodiment of the invention.

DETAILED DESCRIPTION OF SPECIFIC EMBODIMENTS

Definitions. As used in this description and the accompanying claims, the following terms shall have the meanings indicated, unless the context otherwise requires:

"Target" may be any molecule, nucleic acid, protein, virus, cell, or cellular structure of interest.

"Microfluidic array" refers to any ordered structure for holding liquid samples of 100 nanoliters or less.

Embodiments of the present invention are directed to devices and methods for assaying sample liquids using a microfluidic sample array. For example, various techniques for encasing, loading, stacking, thermal cycling and imaging of a microfluidic sample array are presented. Other embodiments of the present invention include adapting individual through-holes of the sample array for capture, chemical processing of captured targets, and/or multi-functional processing of liquid samples. Various examples and embodiments are discussed in detail below.

Encased Microfluidic Array

Figure 1:
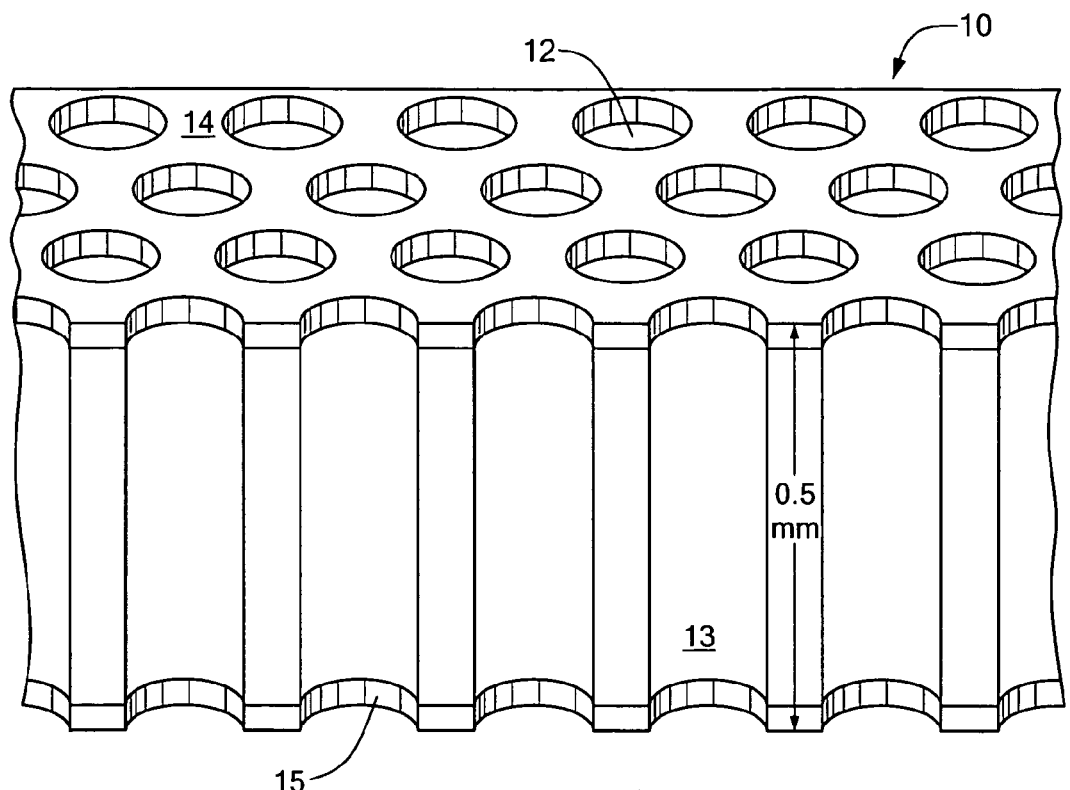
FIG. 1 is a diagram illustrating a typical sample array of through-holes according to prior art.
Figure 2:
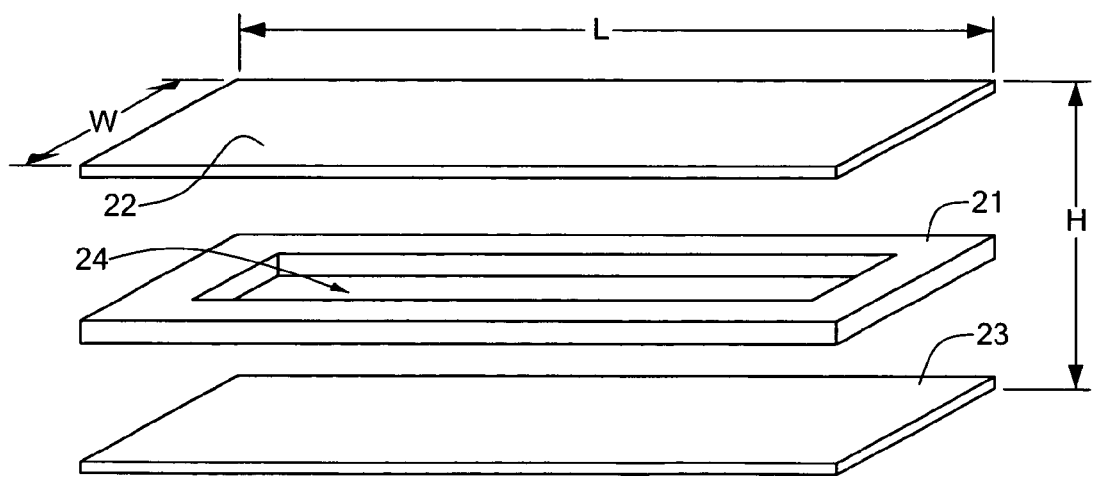
FIG. 2 is an exploded perspective view of a case for a sample array, in accordance with an embodiment of the present invention.

FIG. 2 is an exploded perspective view of a case for a microfluidic sample array, which may be include a plurality of through-holes and/or wells, in accordance with an embodiment of the present invention. The case includes a frame 21, a top 22, and a bottom 23 that, in operation, are placed in sealed relationship to one another such that the case is substantially tight to liquids, and in preferred embodiments, impermeable to low surface energy fluids that are immiscible with water, such as mineral oil or perfluorinated liquids. Under these conditions, the foregoing components define an interior volume 24, into which may be placed a microfluidic sample array.

At least one of the top 22 and the bottom 23 may be advantageously light transmissive, and in various embodiments both the top and the bottom are light transmissive. Light transmissivity of the top and/or the bottom facilitates optical reading of individual through-holes of the array when the array is placed in the interior volume 24 of the case. To prevent fogging, the at least one top 22 or bottom 23 may be coated with a hydrophilic layer.

In some embodiments it is desirable that the case of FIG. 2 have the approximate dimensions of a microscope slide, namely, 25 mm×75 mm×<2 mm (corresponding to dimensions W×L×H shown in FIG. 2) so that the case may be handled by microscope slide handling equipment. To facilitate automated handling of the case, it is desirably that the case be mechanically robust. Moreover, it is often useful to place what shall be called an "encapsulation fluid" in the interior volume with the microfluidic array. The encapsulation fluid assists in providing isolation between through-holes of the array, prevents evaporation of samples, and may help to maintain a uniform temperature throughout the array. This fluid is desirably immiscible with water and substantially unreactive with reactants and analytes that may be placed in through-holes of the array. Typical encapsulation fluids that may be used alone or in combination include, without limitation, mineral oil, silicon oil, and a perfluorinated hydrocarbon or mixture of perfluorinated hydrocarbons, such as perfluorinated alkane (such as Fluorinert from 3M, sold for use as electrical testing fluid), or perfluorinated polyether (available, for example, under the brands Fomblin® and Krytox®, from Solvay Solexis (Thorofare, N.J.) and DuPont (Wilmington, Del.) respectively, and sold for purposes including vacuum pump lubricants). In various embodiments, it is desirable that the encapsulation fluid have a specific gravity greater than 1. In various embodiments, the case is desirably sealed when subjected to assay conditions that may include thermal cycling and, potentially, chemical reactions, that may produce internal pressure changes, and the case is desirably dimensionally stable over the range of expected pressure change. It may be desirable that the encapsulation fluid remain a liquid over the temperature range of the assay which would require that it is substantially non-volatile at room temperature, have a freezing point that is less than room temperature and have a boiling point greater than the highest temperature used in an assay (typically 95° C. for PCR). The halogenated fluids typically permit less evaporation of the samples than the other fluids and are particularly useful for PCR.

As discussed in further detail below, in many instances it is desirable to form the case in such a way that one of its six sides remains open so as to permit insertion into the interior volume of the array and sealing after the array has been inserted. A convenient way of doing this is to make the frame 21 in a U-shape, for example, with the frame open along one side of its width to permit insertion of the array. After the array is inserted, the remaining leg of the frame (and open side of the case) may be sealed. Alternatively, a slot may be formed in one side of the frame that permits insertion of the array, which can then be sealed, or otherwise closed, after insertion of the array.

The frame 21, top 22, and/or bottom 23 may be coupled together to form the case by, without limitation, at least one of an epoxy or other adhesive. In various embodiments, the frame 21 may be implemented as a gasket (for example, of closed-cell acrylic foam) which may work under compression and/or be provided with adhesive on both sides to adhere to the top 22 and bottom 23, which may suitably be made on either top 22 or bottom 23 of glass, or a polycarbonate plastic. One of the top 22 or bottom 23 may be made of an opaque material such as a metal, with the other side permitting optical readout. The opaque part may be advantageously made from a heat conducting material such as stainless steel, which may be placed adjacent a heat source, such as a Peltier device, during thermal cycling.

The geometry of the case in relation to the array is often important to the design and implementation of the system. For example, the gap between the array and the case, and surface treatment on both sides of the array can affect: the ability to load the sample into the chip in situ; the formation and behavior of gas or vapor bubbles during thermal cycling; and whether the gas bubbles that may be generated can cause sample evaporation with resulting condensation of water vapor on the case or chip surfaces.

To ensure proper separation between the array and the case, the surfaces of the top 22 and the bottom 23 which face the interior volume 24 may be equipped with a spacing means such as shims, bumps, and or posts protruding from them so that the array does not contact the surfaces. Alternatively, the array itself may be provided with shims, bumps, and/or posts on its faces so that the sample does not contact the surfaces of the top 22 and bottom 23 that face into the interior volume 24. In various embodiments, spacing may be achieved by providing a mixture of glass beads in glue that is applied to select locations on the array. In other embodiments, the array may be fabricated with suitable spacing elements formed of the array material itself to provide any desired spacing between the bulk of the array and the inner facing portions of the top 22 and bottom 23.

Figure 3A:
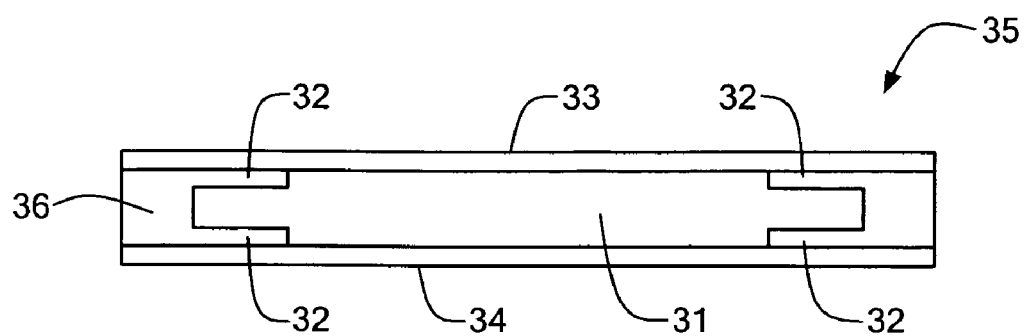
FIG. 3(a) is a diagram illustrating a top view of a case that includes a U-shaped frame with centering guide rails, in accordance with an embodiment of the invention.
Figure 3B:
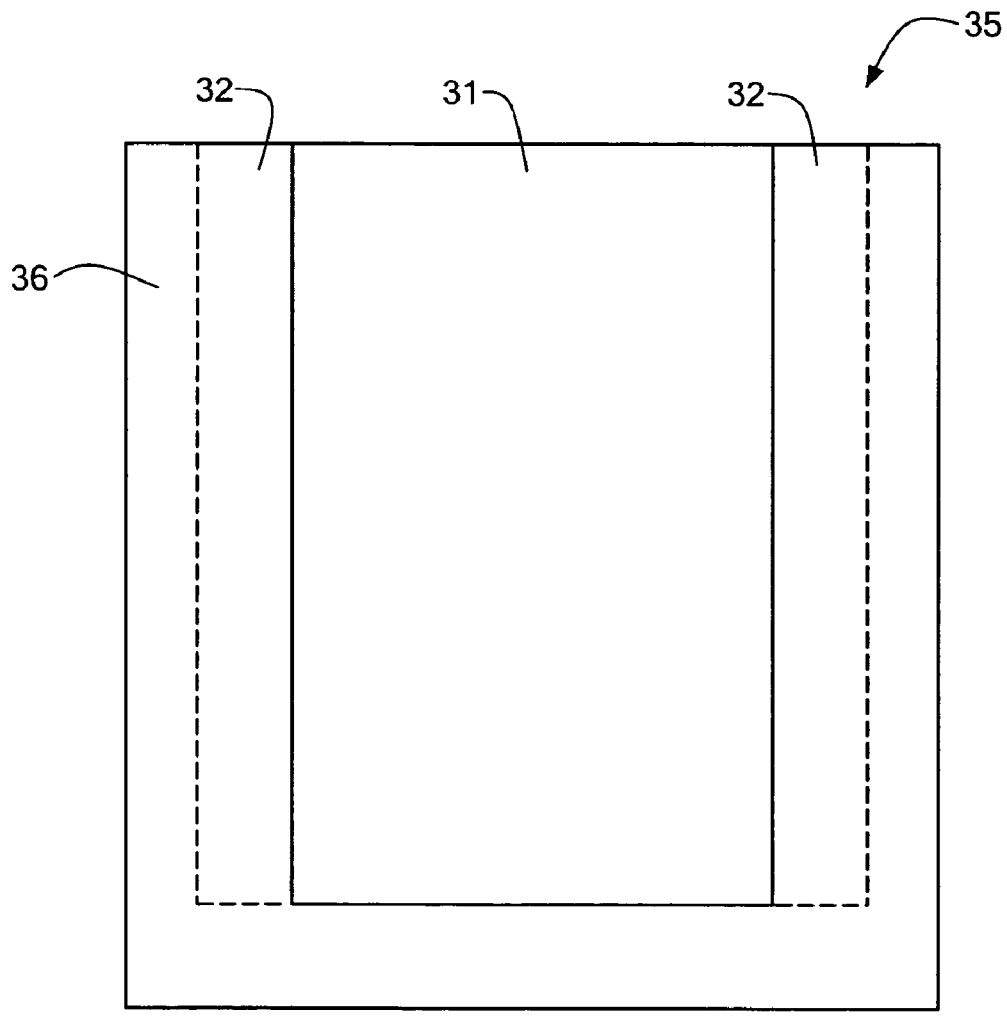
FIG. 3(b) is a diagram illustrating a side view of the case shown in FIG. 3(a), in accordance with an embodiment of the invention.

FIGS. 3(a) and 3(b) shows a top view and a side view, respectively, of a case 35 that includes a U-shaped frame 36 with centering guide rails 32, in accordance with one embodiment of the invention. In various embodiments, the centering guide rails 32 may be attached or integral to the covers 33, 34 or the frame 36, or both. The centering guide rails 32 securely hold the sides of an inserted array in between a left cover 33 and a right cover 34. In one specific embodiment, the through-holes of the array are held in position without touching either the left cover 33 or the right cover 34. The concept of left and right covers 33 and 34 suggests that the case 35 possesses a vertical orientation. In other embodiments, the case 35 may have a horizontal orientation (in which case the covers would correspond to the top 12 and bottom 13 of FIG. 2), or a hybrid orientation.

Preparing and Loading the Microfluidic Array

Figure 4:
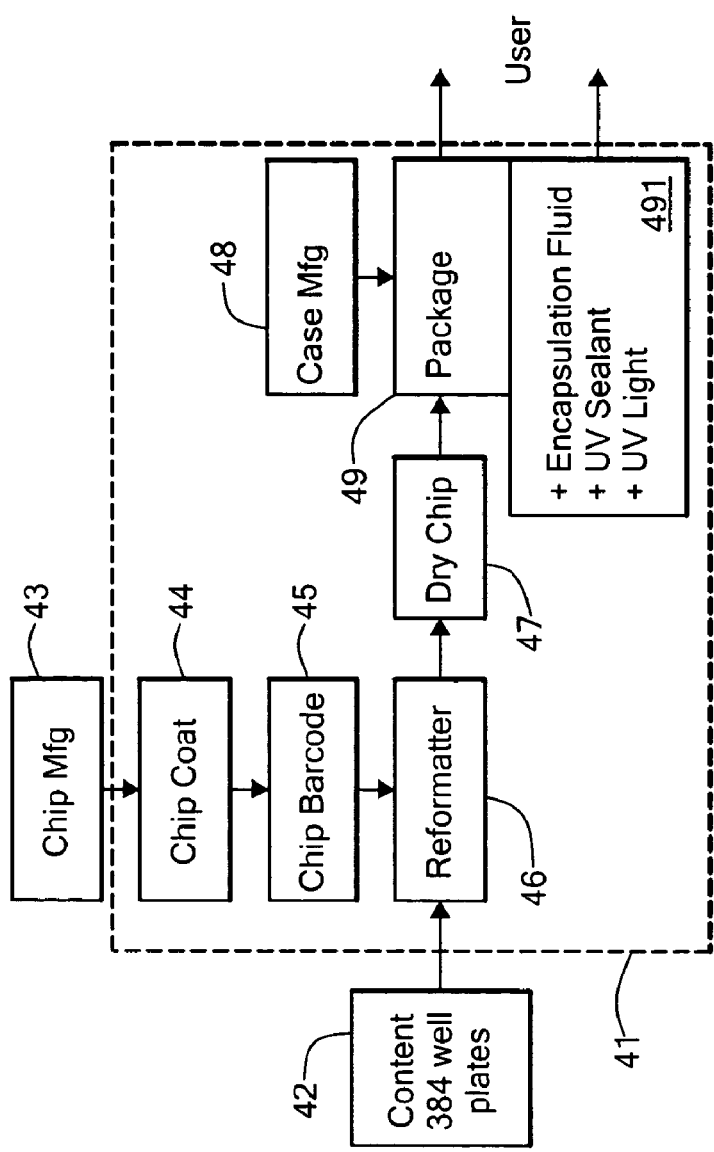
FIG. 4 is a block diagram of a method for providing a system including an array, a case, and related components so as to permit a user to perform assays, in accordance with an embodiment of the invention.

FIG. 4 is a block diagram of a method in accordance with the present invention for providing a system including a microfluidic array, a case, and related components so as to permit a user to perform assays using the system. The processes enclosed by dashed line 41 are typically performed by the supplier of the assay system. In process 42, the supplier is provided with content to be introduced into through-holes of the array, and here it is provided in a plate having 384 wells. The content may be reactants, and alternatively, or in addition, may include, for example, samples, standards, or analytes. Meanwhile, in process 43, the supplier is also provided with the array in a raw form as a sheet of material, for example, of silicon or steel in which throughholes have been formed. In process 44, the array is treated, for example with hydrophobic and hydrophilic material, and in process 45 appropriately barcoded. In process 46, the array is populated with the content derived from the plates obtained in process 42. In process 47, the array is dried in preparation for packaging which occurs in process 49. In process 48, meanwhile, a suitable case is prepared as discussed previously in connection with FIG. 2. In this circumstance, the case is prepared with an open side as discussed above. The user receives a system that includes the array, stored in the case, encapsulation fluid as discussed above, and an arrangement for sealing the case after the array has been further populated by the user. For example, the sealing arrangement may include a sealant that is activated by ultraviolet light, as well as a source for the ultraviolet light used to activate a sealant. The supplies of the fluid, sealant and light, are indicated by box 491.

FIGS. 5 through 16 are diagrams illustrating an embodiment by which a user may perform assays using the system described in connection with FIG. 4.

Figure 5:
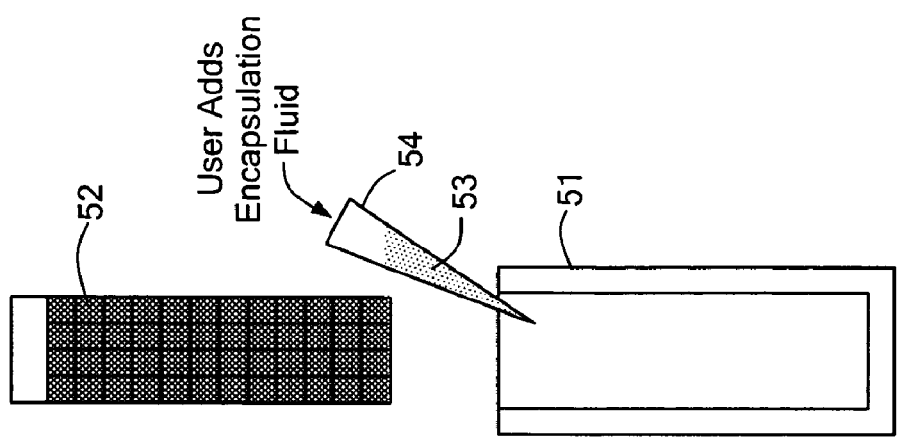
Figure 6:
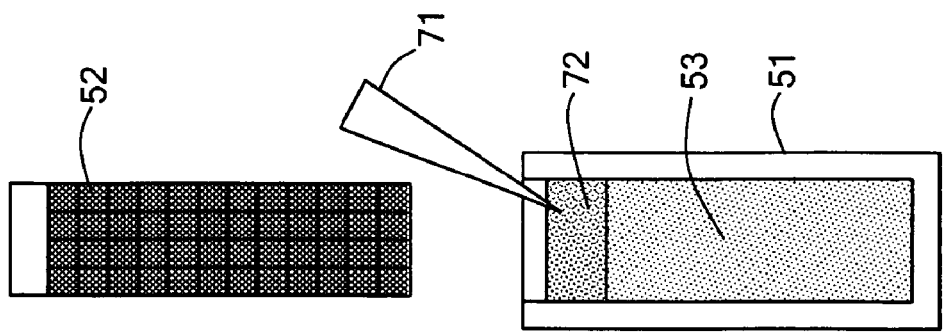

FIG. 5 and FIG. 6 are diagrams illustrating the addition of an encapsulation fluid 53 to a case 51, in accordance with an embodiment of the present invention. An array 52 is depicted outside of the case 51. In FIG. 5, encapsulation fluid 53 is provided in a dispenser 54, which may be, for example, a syringe or similar equipment. Using the dispenser 52, the encapsulation fluid is added to the case 51, as shown in FIG. 6.

Figure 7:
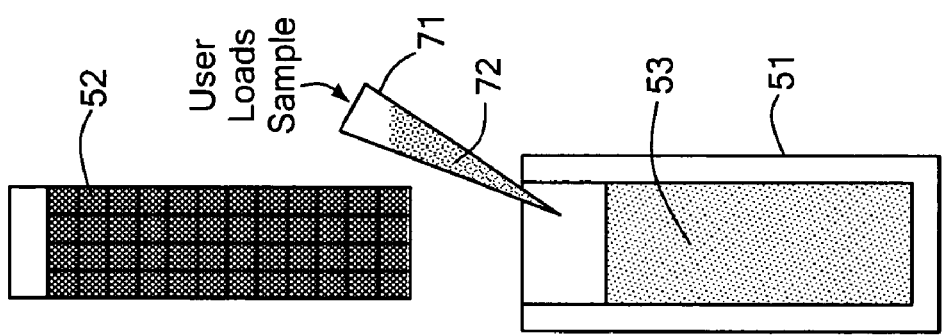
Figure 8:
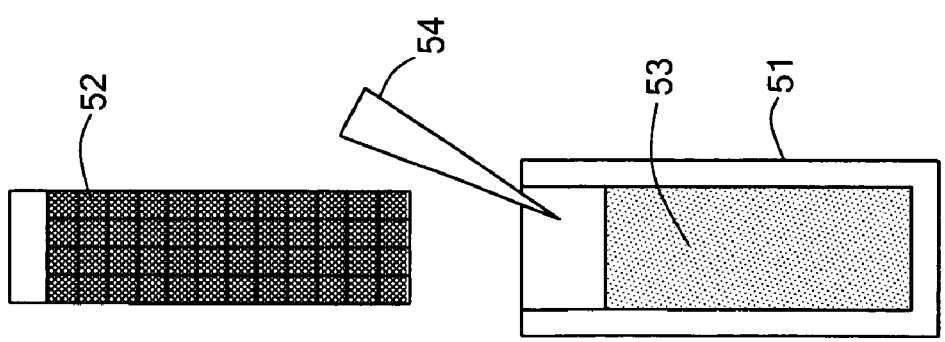

FIG. 7 and FIG. 8 are diagrams illustrating the addition of sample 72 to the case 51 of FIGS. 5 and 6 after the encapsulation fluid 53 has already been added, in accordance with an embodiment of the present invention. In FIG. 7, the encapsulation fluid 53 is shown in the case 51, and a dispenser 71 (which may again be implemented as a syringe or similar device) is used to load sample 72 into the case 51. In FIG. 8, the sample 72, being aqueous based, is shown lying above the encapsulation fluid 53, which has a specific gravity greater than 1.

Figure 9:
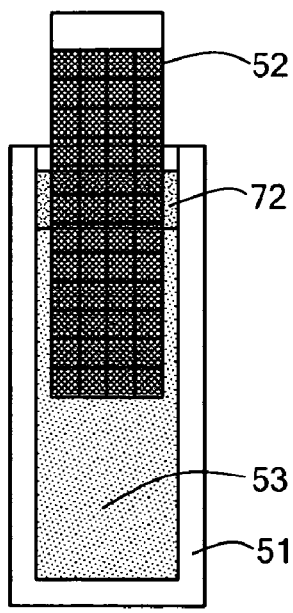
Figure 10:
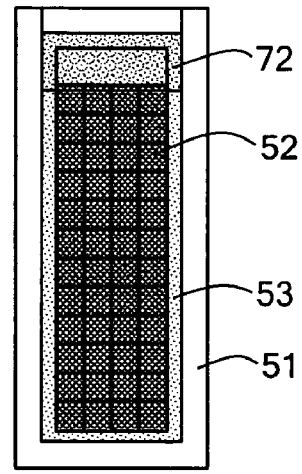

FIGS. 9 and 10 are diagrams illustrating the insertion of a microfluidic array 52 into the case 51 of FIGS. 5 and 6 in accordance with an embodiment of the present invention. In FIG. 9, the array has been inserted part way, and it can be seen that before any through-hole of the array 52 reaches the encapsulation fluid 53, it is passed through sample 72 where it may engage the sample 72. In FIG. 10, the array 52 has been fully inserted into the case 51, and all through-holes of the array have passed through the sample 72. At this point, the through-holes of the array 52 are fully populated.

Figure 11:
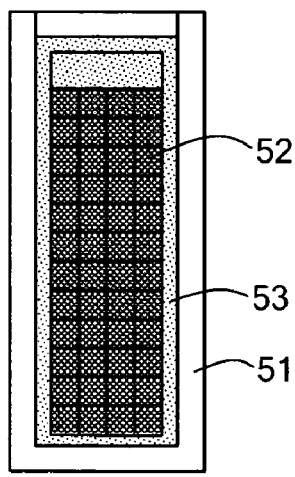

After the array 52 has been full inserted into the case 51, any excess sample is removed. FIG. 11 is a diagram illustrating removal of excess sample (shown as item 72 in FIG. 10) from the case 51, in accordance with an embodiment of the present invention. Since the sample 72 lies on top of the encapsulation fluid 53, as shown in FIG. 10, the excess sample may be removed in a straightforward manner.

After the excess sample has been removed from the case 51 as shown in FIG. 11, the case 51 can be sealed. In various embodiments, the case 51 may undergo further processing prior to sealing. For example, the case may be thermally cycled before sealing, as described in more detail below. If kept in a vertical position throughout the analysis, sealing may be avoided entirely, although the case may be prone to spillage.

Figure 12:
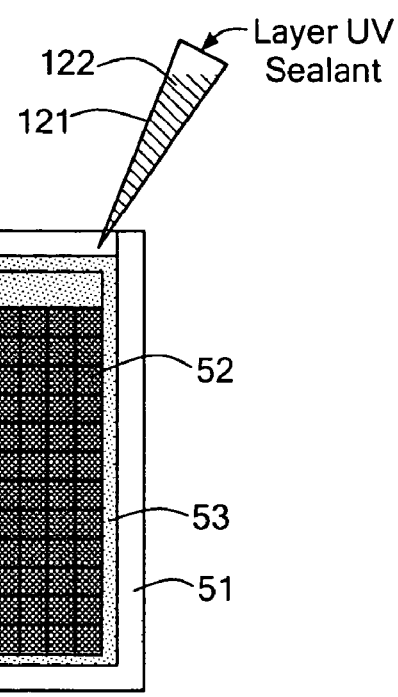

FIGS. 12 and 13 are diagrams illustrating the application of a sealant 122 to the case 51, in accordance with an embodiment of the present invention. A dispenser 121 may be used to dispense sealant 122 to the open side of case 51.

The sealant illustrated here is cured by exposure to ultraviolet light. Accordingly, FIG. 14 is a diagram illustrating the use of ultraviolet light to cure the sealant applied in the manner illustrated in FIGS. 12 and 13, in accordance with an embodiment of the present invention. Here an ultraviolet light source 141 provides ultraviolet light (illustrated schematically as item 142) to the sealant to cause it to be cured. Alternative sealants, which are not cured by ultraviolet light, may also be employed. In various embodiments, the sealant is a suitably thick and inert substance, such as a high vacuum grease. Suitable high vacuum greases may include silicone, and also perfluorinated polyether/PTFE substances, such as Fomblin® VAC™ 3, a perfluoropolymer based vacuum grease thickened with a PTFE thickener, from Solvay Solexis (Thorofare, N.J.). Alternatively, a suitable wax may be used in appropriate circumstances.

FIG. 15(a) is a diagram illustrating the case 51 after sealing. As an alternative to the loading arrangement just described, the array may be, placed in the case, and sample added to the case to fill the array, excess sample removed and then encapsulation fluid can be added through one or more open sides or injected directly through the frame material if it is a self-sealing material. To provide self-sealing properties, a gap in the frame material may be filled with a second material, such as vacuum grease. In such a case, encapsulation fluid may be dispensed through the grease using a syringe, with the vacuum grease sealing the hole created by the syringe's needle after the needle is withdrawn.

FIG. 15(b) is a diagram illustrating a top view of a case 155 that includes a resealable grease lock, in accordance with one embodiment of the invention. The case 155 includes a frame 158, a top cover and bottom (not shown). The frame 158 may be a gasket that is made from, without limitation, an acrylic foam or other suitable material that can be penetrated by a syringe or other dispenser. The frame 158 includes a hole 159 that is filled with grease or other self-sealing material, the hole 159 becoming enclosed when the frame is coupled to the top 157 and bottom to form the case 155. Fluid, such as encapsulation fluid 153 may then be dispensed through the frame 158 and grease-filled hole 159 using a syringe. Upon removal of the syringe, the self-sealing grease-filled hole 159 sufficiently seals the interior volume defined by the case 155. The resealable grease lock 156 may be in addition to a sealable opening on one side of the case 155 that can be used for inserting an array 152, as in above-described embodiments. Alternatively, the array 152 may be positioned within the interior volume of the case 155 during case 155 formation.

FIG. 16(a) is a diagram illustrating an embodiment of the present invention enabling the introduction of a sample into through-holes of a microfluidic array, in accordance with an embodiment of the present invention in which turbulence is introduced into the case. The array 162 may be sealed in a case 161 with both encapsulation fluid 163 and an aqueous sample 165, or aqueous sample alone. By causing the array 162 or sample to move back and forth, samples such as nucleic acids or proteins may be loaded into the chip. If a capture probe (described in more detail below) is included in through-holes of the array 162, the reciprocation will cause mixing of the sample and more rapid capture in through-holes of the array 162, which may be followed by an amplification such as PCR or ELISA. The fluid is desirably perfluorinated liquid and more dense than the sample, and thus the mixing, which may be done in combination with thermal cycling, is done preferably with the case in the vertical position with the array 161 at the bottom. The mixing may be effected by rocking, tumbling or spinning the case. The array 162 may be moved back and forth by other methods such as including magnetic materials in its construction (e.g. the array 162 itself or magnetic beads adhered) and dragging the array with a nearby magnet. The magnetic dragging mechanism may be integrated into a thermal cycler device. Structures may be placed on the array 162, such as beads or posts, which cause turbulent mixing to occur as the array 162 is dragged back and forth. This embodiment has the advantages of using a relatively low volume of liquid sample, reducing the number of steps necessary for loading/concentrating, being less error-prone in that a minimum of chip handling is done and convenience due to automation.

FIG. 16(b) is a diagram illustrating the introduction of a sample into through-holes of a microfluidic array by rotating the array, in accordance with an embodiment of the present invention. The array 165 is mounted in a tube 166. The tube 166 is then filled partly with sample and placed on a vertically oriented rotating disk (not shown). The rotation 167 of the disk forces the sample to flow repeatedly through the array 165, resulting in rapid sample concentration within the through-holes of the array 165. In other embodiments, the array 165 can be mounted to a bracket molded into the top of a screw cap, and then the cap can be attached to a plastic tube containing the sample to be analyzed. In still other embodiments, the array 165 may be sealed in a case with both encapsulation fluid and an aqueous sample 165, with the case attached to the rotating disk.

Figure 17:
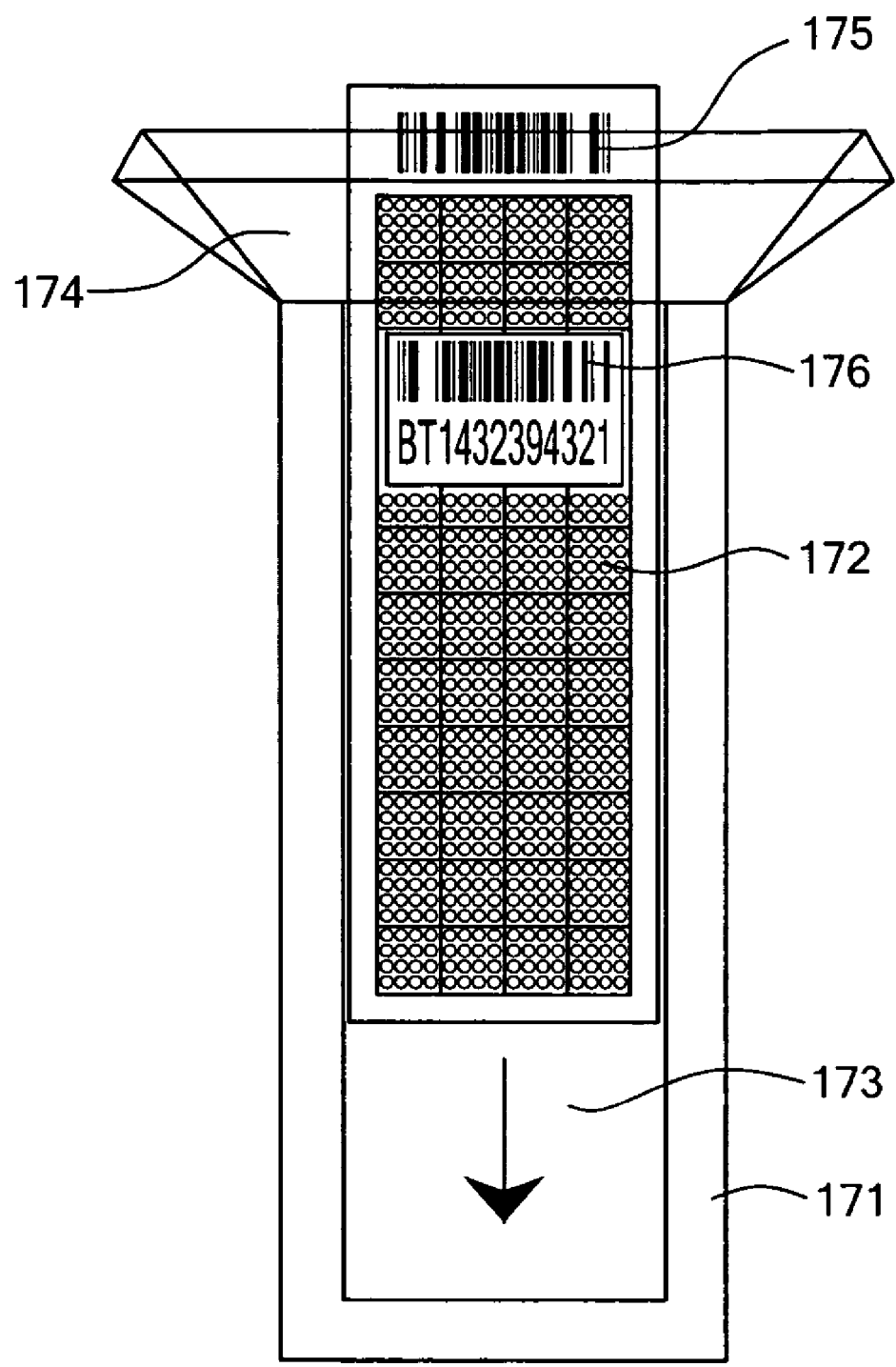
FIG. 17 is a diagram illustrating an embodiment of the present invention facilitating the introduction of sample into through-holes of a microfluidic array via a funnel, in accordance with an embodiment of the present invention.

In further embodiments, a system and method for minimizing the volume of sample needed during loading of the array is provided. One limitation with the method described in FIG. 7 and FIG. 8 is that as the array 52 is lowered through the sample 72, the filling of the array 52 will reduce the volume of sample 72. If the total sample volume in the case 51 is lower than a critical value, the sample 72 will not remain as a horizontal layer as the array 52 passes through it, but will recede from the edges and assume the form of a droplet or droplets in or on top of the immiscible fluid. Thus, not all through-holes of the array may be populated with sample 72. Since the volume of sample 72 used must be enough to ensure that the total sample volume in the case 51 is higher than the critical value, this method may be costly in terms of the amount of sample 72 needed. Accordingly, various embodiments may advantageously ensure that the sample 72 remains spread in the form of a thin layer that extends across the width of the case 71 during the entire loading procedure. Such spreading means may be, for example, a region of hydrophilic material created on a background of hydrophobic material on the walls of the case 71. For example, the case 71 sides may be made from glass that has been silanized with OTS (octadecyl trichlorosilane) and then masked and exposed to a UV light to create hydrophilic stripes. These hydrophilic stripes may be rendered biocompatible by further treatment such as with a PEG-silane. In another embodiment, the spreading means may be in the form of a comb or brush, the sample retained in a stripe formed by fingers or bristles. FIG. 17 is a diagram illustrating an embodiment of the present invention facilitating the introduction of sample into through-holes of a microfluidic array 172, in accordance with an alternative embodiment of the present invention. In this embodiment, a funnel guide 174 is provided in contiguous relationship with the case 171. In this fashion, the introduction of sample material, in the manner discussed in connection with FIGS. 7 and 8 is facilitated and the minimum volume of sample needed is reduced. In various embodiments, the funnel guide 174 is integrated into the case 171. Alternatively, the funnel guide 174 may be a separate or removable item.

The funnel guide 174 may be of various shapes and sizes. For example, in one embodiment the funnel guide 174 may take the form of a trough with a narrow slit. The slit is of a narrow enough width such that sample will not pass through it when sample is placed in the funnel guide 174 above. The slit allows the array 172 to pass through it into the case 171 situated below. In a preferred embodiment, the slitted trough is made of a flexible material such as thin plastic that deforms to allow the array 172 to pass through the slit. The thin plastic provides slight contact and pressure against the array 172, preventing sample from leaking out of funnel guide 174 as well as facilitating sample loading in the array 172 and removal of excess sample on the array 172. As the user passes the array 172 through the sample and slit, the array 172 will fill with sample and pass into the case 171. If the case 171 is filled with encapsulation fluid 173 prior to insertion of the array 172, the amount of time that the filled array 172 is exposed to air and the amount of evaporation of the samples is advantageously minimized.

In order to further facilitate the entrainment of sample in the through-holes of the array 172, the funnel guide 174 may be provided with a series of fine brushes past which the through-holes of the array 172 move, with the result that, by capillary action, the sample in the funnel guide 174 is quickly guided into the through-holes. Note that the brushes may be used independently and/or regardless of the shape of the funnel 174, with the effect of spreading the sample out vertically and thus minimizing the amount of sample needed.

In FIG. 17, both the array 172 and case 171 are identified via barcodes 175 and 176, respectively. Other means of identification may be also be used as known in the art, such as printed labels that vary in color or shape, or smart labels having radio frequency transponders.

Thermal Cycling/Analysis

Figure 18:
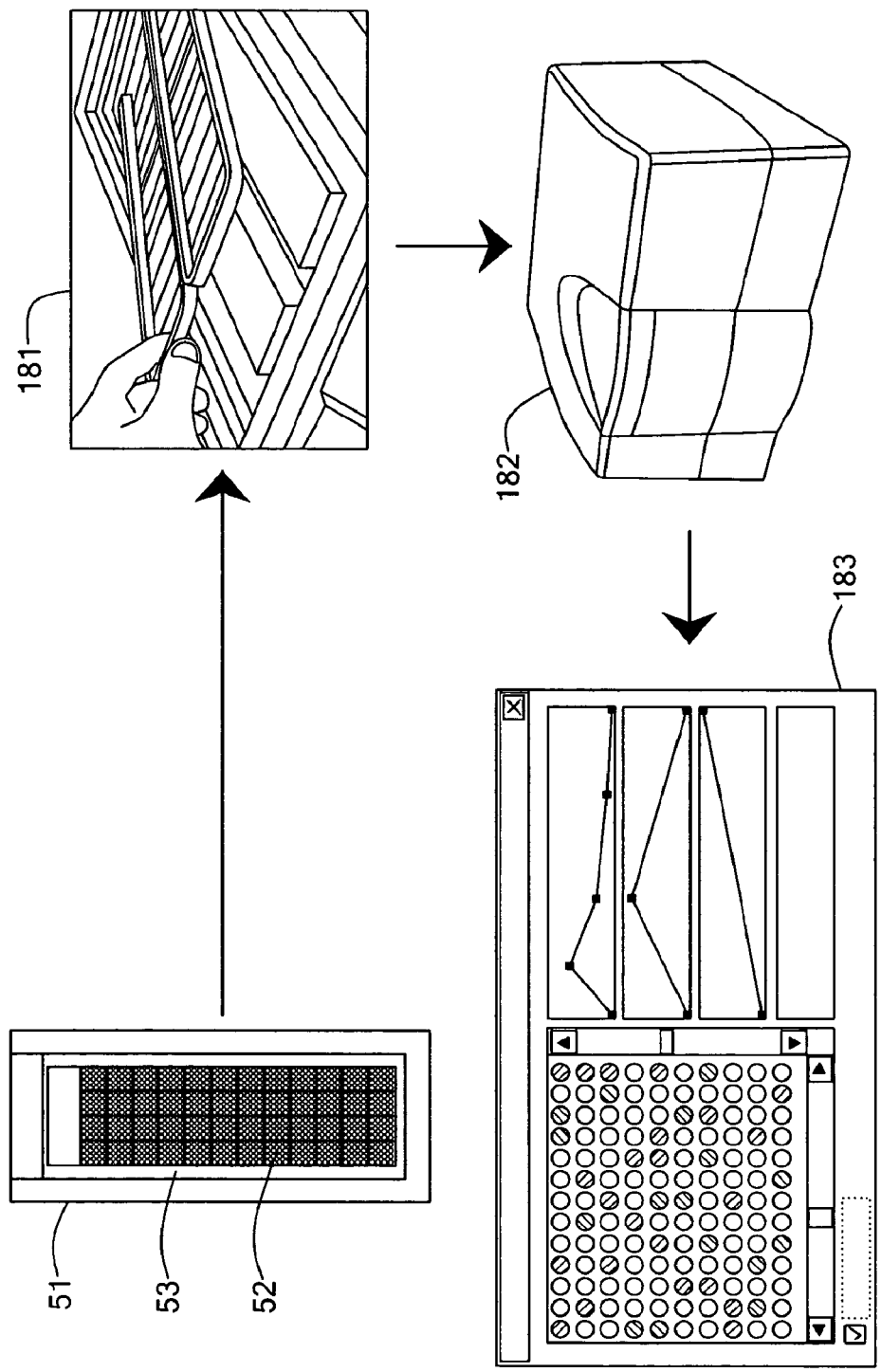
FIG. 18 is a diagram illustrating use of the sealed case of FIG. 15 in a thermal cycler, and in a scanner, so as to provide data that is subject to analysis in analysis software, in accordance with an embodiment of the present invention.

FIG. 18 is a diagram illustrating use of the sealed case of FIG. 15 in a thermal cycler 181, and in a scanner 182, so as to provide data that is subject to analysis using analysis software 183, in accordance with an embodiment of the present invention. In this fashion, the contents of each of the through-holes in the array may be cycled through alternating temperatures and subjected, for example, to analysis using Polymerase Chain Reaction (PCR) or Deoxyribonucleic Acid (DNA) sequencing techniques.

In various embodiments of the present invention, the thermal cycler 181 may be based, without limitation, on a temperature controlled circulating fluid or a temperature controlled thermal block. Both of these approaches are further described below.

Thermal Cycler with Circulating Fluid

Figure 19:
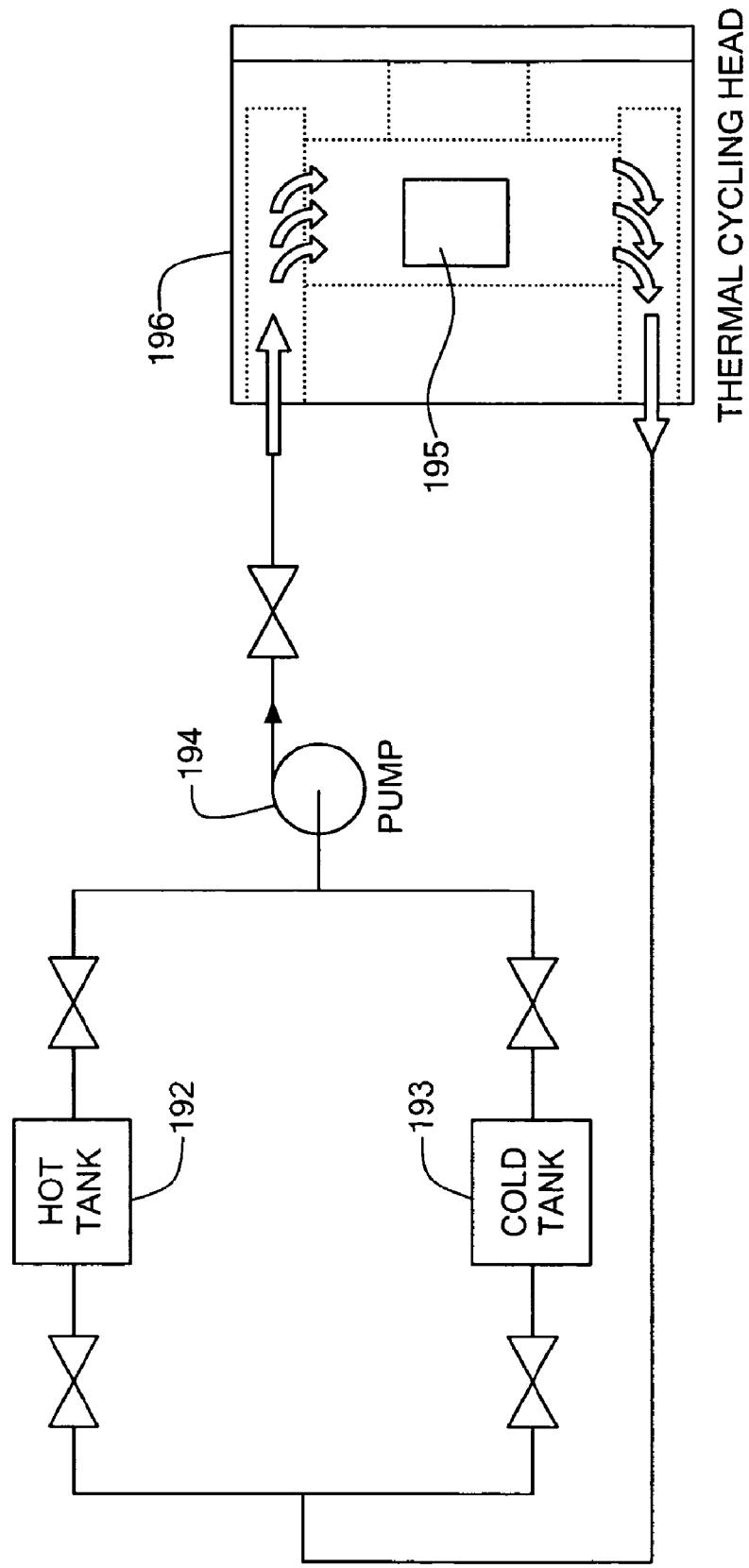
FIG. 19 is a diagram illustrating a thermal cycling system, in accordance with an embodiment of the present invention.

FIG. 19 is a diagram illustrating a high-density microfluidic thermal cycling system, in accordance with one embodiment of the invention. A case 195 containing an array, as described in above embodiments, is inserted into a thermal cycling head 191 that safely immerses the case 195 in a bath of controlled-temperature circulating fluid. A good circulating fluid possesses a high heat capacity, and specific examples include air, water and silicone oil. The cycling head 191 receives a circulating flow of fluid at a controlled temperature pumped from one of a hot tank 192 or a cold tank 193 by circulating pump 194. A valving arrangement allows for alternating selection between the two controlled-temperature storage tanks. Although FIG. 19 shows separate inlet and outlet valves for each tank, equivalent valving arrangements can be used, including valve manifold arrangements and multi-port valves, any of which may operated manually, pneumatically, or electrically.

The temperature of the fluid circulated through the cycling head 191 and past the case 195 is rapidly imparted to the array, allowing near-instantaneous temperature change to be uniformly applied to a large number of samples. For example, one embodiment processes 25,000 parallel PCR reactions simultaneously by producing 40 thermal cycles per hour.

The case 195 holding the array may be loaded by sliding it into a slot opening 196 in the cycling head 191, for example along a guide rail arrangement that holds the sealed case 195 in position in the flow of circulating fluid. Such an arrangement allows for vertical orientation of the case 191 and array (as shown, for example, in FIG. 15), which is not possible in prior art thermal cycling systems that are restricted to horizontal positioning of the array. Orientating the array vertically can be advantageous, for example, in preventing bubbles from getting stuck underneath the array, described in more detail below.

Figure 20C:
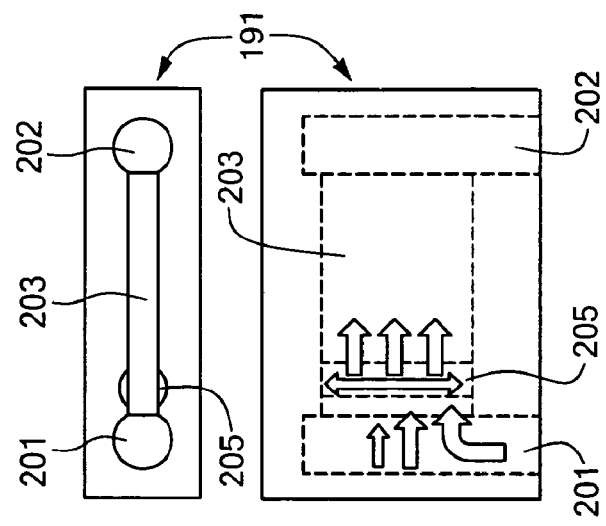
FIGS. 20(a-c) are diagrams illustrating structural details of various specific cycling head embodiments, in accordance with various embodiments of the present invention.
Figure 20B:
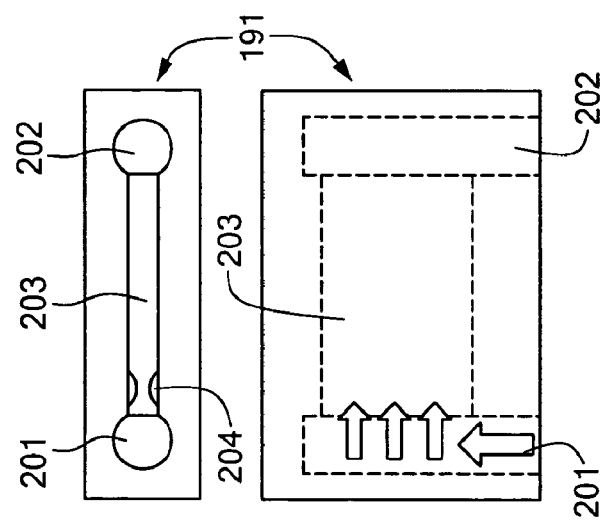
Figure 20A:
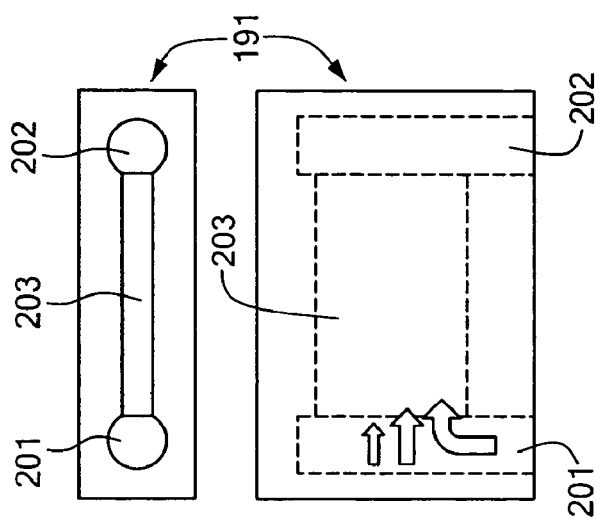

In some specific embodiments, the specific geometry of the cycling head 191 and specific mass flow rates of the circulating fluid could result in non-uniform fluid flow across the case 195. For example, as shown in FIG. 20(*a*), if the inlet port 201 and outlet port 202 of the thermal cycler 181 are smooth-bore cylindrical chambers, and if the connecting flow channel 203 has simple planar walls, the circulating fluid may flow preferentially across the portion of the case that is closest to the opening of the inlet port 201. This can be undesirable since it results in uneven temperature gradients across a case 195 that is inserted into the flow channel 203.

Such flow irregularities can be addressed by a flow regulator structure, which may be implemented in a variety of ways. FIG. 20(*b*) shows use of a flow restrictor 204 on the inlet side of the flow channel 203, towards the opening end of the inlet 201 to ensure even flow through the fluid channel. One variation of such a flow restrictor 204 utilizes one or more ridges added to the walls of the flow channel 203 to restrict the flow of fluid nearest to the opening of the inlet port 201. Such an arrangement minimizes eddies and dead zones in the flow, and promotes laminar flow of fluid in a uniform sheet over the case 195. This also helps create a more uniform temperature and to prevent bubbles from forming (which may distort sample imaging).

Alternatively, FIG. 20(*c*) shows a flow inlet cavity 205 upstream of the case 195 and on the inlet side of the flow channel 203 that acts as a flow regulator. The flow inlet cavity 205 may be wider than the case slot 196 and bounded by narrower regions on each side. This arrangement promotes fluid flow equalization across the case 195. Other flow control techniques can be implemented to address this issue, such as a straight-through flow arrangements.

With reference to FIG. 2, the top 22 and the bottom 23 of the case 195, which form the sides of the case 195 when the case 195 is in a vertical position, may be wholly or partly made of glass or other transparent material, and a corresponding section of the cycling head 191 may also be transparent. This allows for real-time imaging during thermal cycling, or convenient imaging before and after thermal cycling. Note that in other embodiments, imaging may be performed when the case 195 has been removed from, or may be independent of, the thermal cycling system.

Referring back to FIG. 19, other embodiments may have more or less than the two controlled-temperature storage tanks 192, 193. Alternatively, some assays may benefit from having three or more tanks at distinct controlled temperatures. Any arrangement of heating or cooling devices could be used to maintain the fluid in each tank at the desired controlled temperature. For example, heating coils and/or cooling coils may be immersed in any of the tanks.

Or there may be only one controlled-temperature storage tank, which is set at the lowest temperature (for example, in PCR or DNA sequencing, this would be the hybridization temperature, 55° C.). Higher temperature cycles could then be achieved by heating the circulating fluid prior to entry to the cycling head 191. For example, a heating coil could be wound around or embedded in a portion of the tubing between the outlet of the pump 194 and the cycling head 191. Instead of a heating coil arrangement, the circulating fluid could flow past one or more heated plates, such as a Peltier device, integrated into the cycling head 191 to heat the fluid. In any of these arrangements, a feedback loop could be used to precisely control the temperature of the circulating fluid.

In such an embodiment, it is advantageous to keep the temperature of the tank or tanks constant, so the fluid exiting the cycling head 191 should be cooled prior to its re-introduction to the tank or tanks. The circulating fluid could be cooled by a coil wound around or embedded in a portion of the tubing between the cycling head 191 and the controlled-temperature storage tank, or a cooling coil arrangement could be provided for the tank, again with a feedback loop to control temperature. Or, cooling plates, such as a Peltier device, could be integrated into the cycling head 191 to cool the circulating fluid as it exits the cycling head.

The advantages of a single tank system include faster heating times, more compact design, and less expense (fewer baths). Expense could be reduced even further by keeping the storage tank at room temp and actively controlling the temperature of the circulating fluid as it approaches the cycling head 191. A single controlled temperature environment could be useful on its own, for example, for drug screening.

In an embodiment having a temperature sensor, feedback control of the temperature signal could be used to automate the system. For example, automatic valve switching could be programmed to occur when a desired temperature is sensed. Such automatic and programmable operation is considered a customary feature of a thermal cycler. An embodiment may also feature automatic generation of melting-curve data by imaging as a function of temperature, e.g., after PCR with SYBR Green (Molecular Probes).

Thermal Cycler with Thermal Cycling Block

Figure 21:
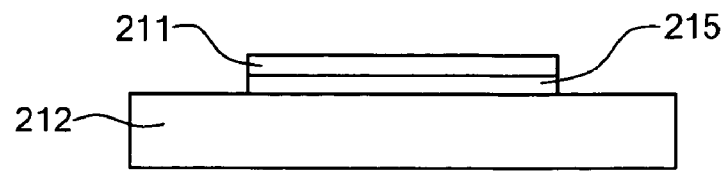
FIG. 21 is a diagram illustrating a side view of a thermal cycling flat block, in accordance with an embodiment of the present invention.

Instead of immersing the case 211 and/or array in a bath of controlled-temperature circulating fluid, the case 211 and/or array may be placed on a thermal cycling block such as a flat-block 212, as shown in FIG. 21, in accordance with one embodiment of the invention. The thermal cycling flat block 212 may be, without limitation, a thermoelectric device, such as a Peltier Effect cooling device, or other commercial available flat block thermal cycler, such as those sold by Molecular Biology Products of Milford, Mass. A Peltier Effect cooling device typically includes P-type and n-type semiconductor material connected electrically in series between two surfaces. When a voltage is applied to the semiconductor material, electrons pass from the p-type material to the n-type material, causing heat to be transferred from one surface to the other. The rate of heat transfer is proportional to the current and the number of p-n junctions.

A problem that occurs in thermal cycling reactions is that the temperature changes in the sample are often limited by the rate at which heat can leave or enter the Peltier device and be transferred to the samples. It is therefore advantageous to include one or more additional thermal contact means between the case and the thermal-cycling block. The thermal contact means may include a means for applying pressure to the case such as clips. Other embodiments that further increase heat transfer include use of a flexible heat transfer pad, grease, or paste. For example, a heat transfer pad 215, grease or paste may be placed between the flat block 212 (or the cycling head if a fluidic thermal cycler is used) and the case 211 holding the array. Flexible heat transfer pads 215, such as sold under the trade name Gap Pad (Bergquist Company, Chanhassen, Minn.), are typically thin sheets of elastomer containing material that enhances heat transfer. For example, the heat transfer pad 215 may be made of, without limitation, the following materials or combination of materials: silicone, graphite, fiberglass and/or assorted polymers. In various embodiments, the pad 215 may have an adhesive on one or both sides, or may be compressible such that pressure can be placed between the case 211, the heat transfer pad 215, and, for example, the thermal block 212, helping to ensure good thermal contact.

Rapid heat transfer is essential for optimal PCR biochemistry and throughput. The case preferably has a high thermal conductivity on the side, for example, that contacts the thermal cycling block and a low thermal mass to increase its responsiveness to changes in fluid flow temperature. The cycling head or flat plate may also have low thermal mass to ensure rapid thermal response time. Either the case, flat plate or the cycling head may include one or more temperature sensing devices such as a thermocouple probe. Additionally, the case may advantageously be made thin to increase the rate of heat transfer and reduce the amount of immiscible fluid needed. Note however, that if the case is too thin relative to the chip thickness, a gas bubble can form during thermal cycling and bridge from the chip surface to the case cover. This gas bubble causes condensation which can interfere with the PCR process and its imaging. Note however, that if the case is too thin relative to the chip thickness then the gap between chip and case may be small enough that a gas bubble that may form during thermal cycling can bridge from the chip surface to the case cover. This gas bubble could then cause evaporation and condensation which can interfere with the PCR process and its imaging.

Limiting Air Bubble Formation

Although horizontal or hybrid orientation of the array is acceptable for many embodiments, vertical orientation of the case 195 advantageously allows bubbles that form in the immiscible fluid in the case 195 to float up rather than getting stuck underneath the array. Such bubbles could distort imaging of the samples, and also can lead to evaporation of the samples within the array, even through perfluorinated liquid. In various embodiments, thermal cycling in a vertical position can be performed before sealing of the case 195 to allow any gas bubbles or vapor that may be a generated to escape before sealing. This contrasts with a horizontal orientation structure, in which an inlet and outlet tube arrangement would be typically used in order to fill the case 195 completely with immiscible fluid, without leaving any air. In alternative embodiments, thermal cycling in the vertical can be performed without sealing of the case since the contents will not spill in this orientation.

Other techniques, with the case 195 in a vertical, horizontal, or hybrid orientation, may also be used to reduce the formation of undesirable bubble formation. For example, the case 195 may be made rigid, such that the case 195 does not expand due to increased temperatures during thermal cycling. Since the volume within the case 195 is held constant, the pressure increases, preventing formation of undesirable bubbles.

In various embodiments, a salt, or other osmolyte, may be added to the sample or other fluids contained within the case. Since the boiling point is elevated by the osmolyte, outgassing of air in the aqueous sample is reduced, along with evaporation of water. The salt may be added, without limitation, to the sample before dipping of the array, or may be introduced during encapsulation. Small molecule osmolytes such as sugars, including glycerol, are generally suitable. Other osmolytes or hydrophilic polymers that do not interfere with the desired reaction can also be used. For example, PEG, polyvinyl pyrrolidone, polyvinyl alcohol, polyacrylates, KCl, NaCl, or Tris buffers may be used. Amino acids, such as glycine, in the range of 0.1M to 3M, but more preferably between 0.2M and 2M, are also suitable. Betaine (an amino acid) at up to about 2M may be used to prevent evaporation and improve PCR reactions on target sequences rich in G-C (as opposed to A-T).

In still further embodiments, the encapsulated fluid may be sparged with various gases such as, without limitation, hydrogen, or a noble gas such as helium. During sparging, a stream of helium bubbles, for example, is passed through the encapsulation fluid so as to sweep dissolved air out of the fluid liquids, thereby limiting the formation of air bubbles during thermally cycling. The helium remains soluble at all the temperatures used in the thermal cycler and so does not create bubbles itself.

Imaging

Figure 22:
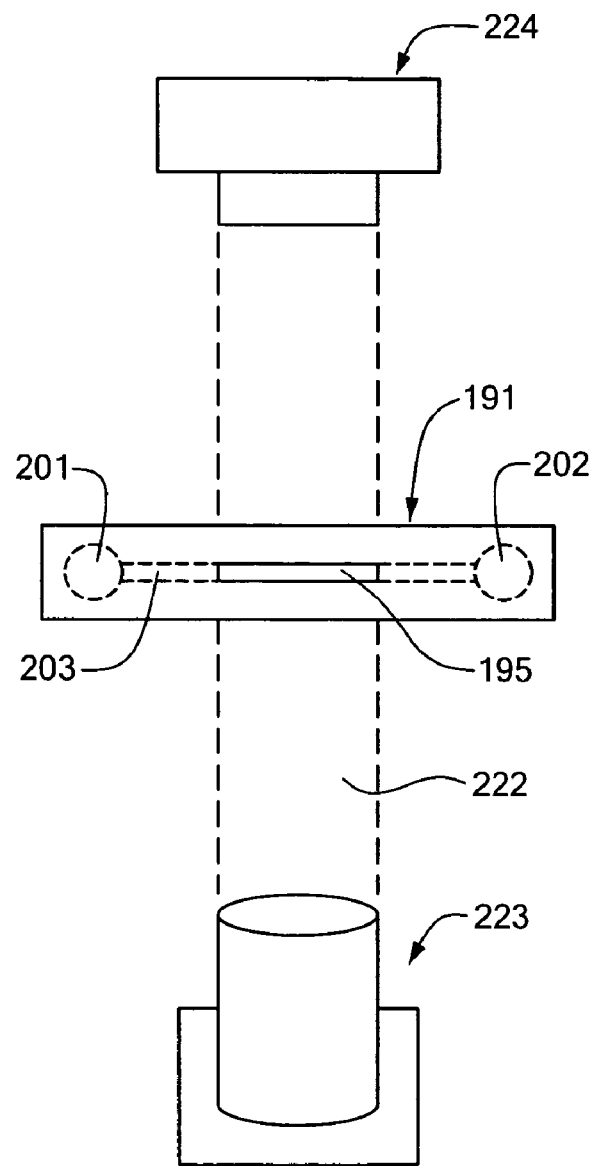
FIG. 22 is a diagram illustrating an imaging system, in accordance with an embodiment of the present invention.

A transmission imaging system may be used where one side of the array, case and/or cycling head is illuminated with white light or other light source, and an imaging sensor (such as a CCD camera) on the other side receives a clear, well-illuminated image of the samples, in accordance with one embodiment of the invention. For example, as shown in FIG. 22, a transmission imaging system may be used where one side of the cycling head 191, or alternatively, just the case 225, is lit by a light beam 222 projected from a light source 223 at appropriate times or temperatures during thermal cycling. The light source 223 may be, without limitation, a white light source such as an arc light, and/or a laser scanning system. The sample through-holes in an array held by the case 225 are thus illuminated, and an imaging sensor 224 (such as a CCD camera) on the unlit side of the cycling head 191 receives a clear, well-illuminated image of the samples. In such a system, the material of the array may be reflective or opaque, e.g., silicon, and the imaging light does not reflect or bleed over into the imaging sensor 224. The illumination of the array may be off-axis from the camera to minimize stray light entering the detector and may be from multiple angles as may be accomplished with the use of mirrors or fiber optic light guides.

In other embodiments of the invention, the imaging sensor 224 is on the same side as the illumination source 223, as for epi-fluorescence imaging. A transparent array material—e.g. glass or plastic, or a opaque and dark material such as an array having black paint on the surface—is thus preferred to avoid reflections reaching the imaging sensor. An optical mask may also be incorporated into the case or imaging system to block light emanating from outside of the channels.

Figure 23:
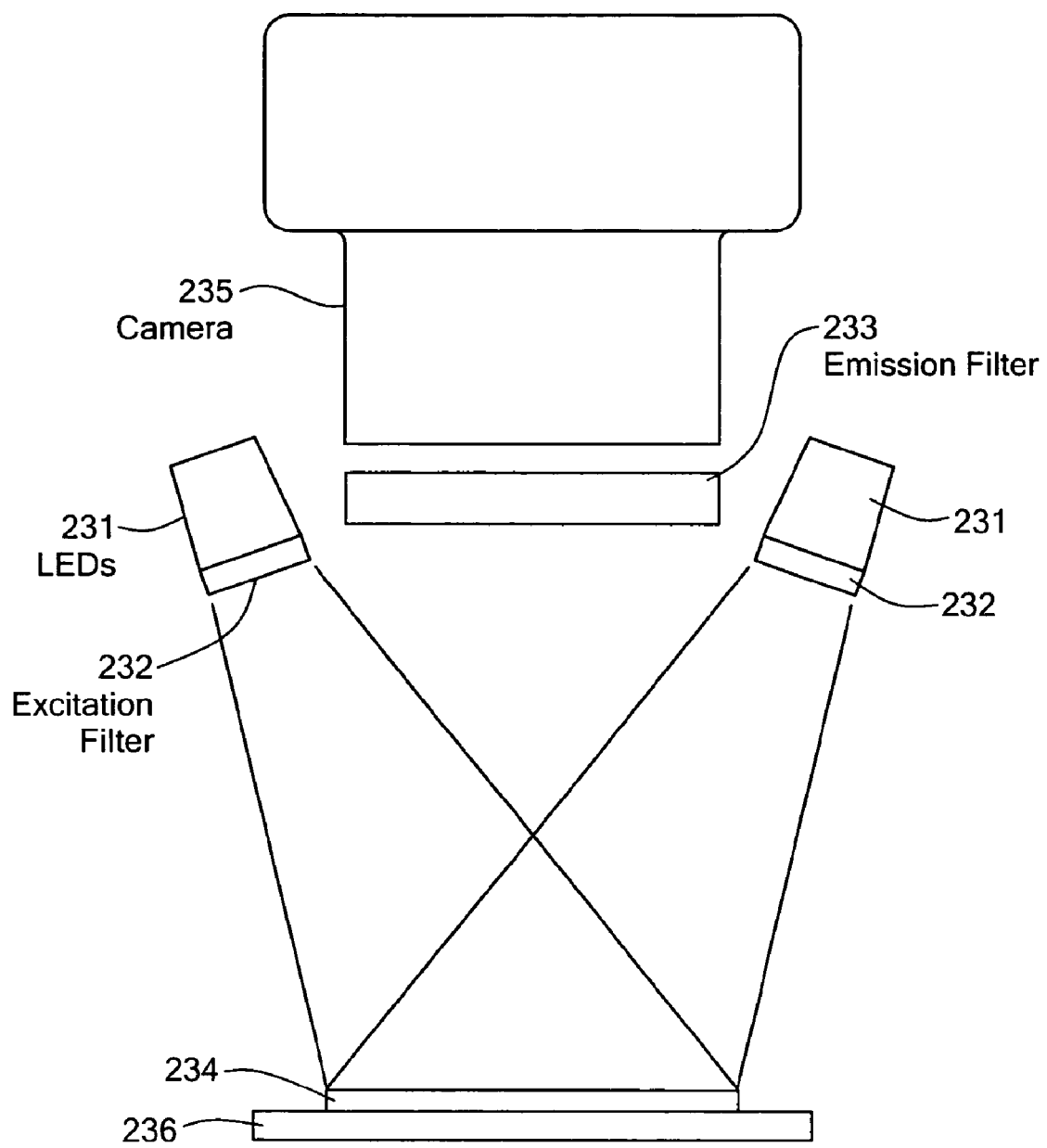
FIG. 23 is a diagram illustrating a transmission imaging system using one or more Light Emitting Diodes (LEDs), in accordance with an embodiment of the present invention.

FIG. 23 is a diagram illustrating a epi-illumination imaging system for illuminating a microfluidic array 234 and the use of one or more Light Emitting Diodes (LEDs) 231 as an illumination source, rather than a white light source, in accordance with various embodiments of the invention. When white light is used, an excitation filter is used to choose the wavelengths that illuminate the sample, and the fluorescence is captured through an emission filter by a camera or other light sensitive device. Instead of a white light source, a bright LED or group of LED's 231 can be used in conjunction with an excitation filter 232. The LED's 231 are chosen by matching their central wavelength to the desired excitation wavelength; since much of the energy produced by the LED 231 is within the excitation spectrum, most of the LED light passes through the excitation filter 232. The sharpness of cutoff for the excitation filters 232 is less important than with white light since most of the light is in the excitation bandwidth, so cheaper filters 232 may be used. Additionally, if the spectrum of the LED 231 is narrow enough, the excitation filter 232 may be removed from the system altogether. Thus, the LED's 231 are more attractive than white light on account of their cost, size, efficiency, and simplicity.

The orientation of the array 234, which may be in a case situated on a thermal cycling flat plate 236 or contained within a cycling head, may be in any orientation with respect to gravity. In various embodiments, a symmetric set of LEDs 231 for each excitation wavelength to be imaged is placed off-axis from the camera 235. The symmetric positioning of the LEDs 231 is often advantageous to avoid shadowing in the three-dimensional through-holes of the array 236. Alternatively, a single set of LEDs may be positioned approximately on-axis that sufficiently illuminates a plurality, or all, of the through-holes of the array 236. Each set of LEDs 231 may include a plurality of LEDs. Alternatively, each set of LEDs 231 may include only a single LED having an output that is sufficient to illuminate a plurality of throughholes, such as, without limitation, a minimum output of 50 mW of radiometric power. The light from the LEDs 231 is columnated, with an angle of divergence from 0 deg to 90 deg. An excitation filter 232 is typically coupled to each LED source 231. The camera 235 is parallel to the surface of the case/array 236 (and/or cycling head 191), and an emission filter 233 is used on either side of the camera lens. A light shaping diffuser may be placed on the output of the LED's 231 to shape the light and provide better illumination uniformity.

The LEDs 231 may provide sufficient lighting to simultaneously illuminate the entire array 236, which may include, without limitation, from 100 to greater than 1600 through-holes and a through-hole density of, for example, greater than one through-hole per 0.25 $mm^2$. During fluorescence imaging for example, the fluorescence from each of the samples in each through-hole may then be simultaneously captured by the camera 235 as a digital image. The camera may be, for example, a Charge-Coupled Device (CCD) or Complimentary Metal-oxide Semiconductor (CMOS) camera, which receives the image from each of the through-holes, or other sample site, simultaneously, and may, for example, transmit or otherwise process the digital image in serial format. Intensity measurements for each sample can then be generated and the intensities processed by analysis software to generate desired data. In various embodiments, a plurality of replication cycles by Polymerase Chain Reaction (PCR) may be performed on the array 236 during thermal cycling, with the entire array 236 being simultaneously illuminated and imaged during each replication cycle.

Polymerase Chain Reaction

In a further embodiment, Polymerase Chain Reaction (PCR) can be performed using very small amounts of genetic material. During PCR, a series of heating and cooling cycles via a thermal cycler is used to replicate a small amount of DNA. Through the use of various probes and/or dyes, the method can be used analytically to determine the presence or amount of a particular nucleic acid sequence present in a sample.

In a specific embodiment, reagents such as primers or fluorescence probes may be immobilized in the through-holes by encapsulation in a wax. This wax is preferably hydrophilic and biocompatible so that it dissolves and releases the reagents upon heating. For example, an array of immobilized primers and TaqMan probes comprising thousands of genotyping or RNA expression assays may be created by encapsulating the primers and probes in polyethylene glycol (PEG) on the walls of the through-holes. The sample containing the nucleic acids to be analyzed is then introduced and the array is thermal cycled with real-time analysis which may be accomplished by the instrumentation described herein.

For genotyping applications, the assay described in U.S. provisional patent application 60/528,461, entitled "Improved Selective Ligation and Amplification Assay" filed Dec. 10, 2003, which has been incorporated by reference in its entirety, provides an advantageous assay system in that many specific and inexpensive assays may be quickly designed. The assay allows for identifying and distinguishing a nucleotide polymorphism in a target sequence of nucleic acid in each through-hole of the array. The assay includes three or more primers, two of which bind to a target nucleic acid sequence, flanking a SNP, so that the 3'-end of one or more first primers is adjacent to the 5'-end of a second primer, the two primers being selectively ligated and then amplified by a third primer to exponentially produce the complementary strand of the target sequence. The other strand of the target sequences is exponentially amplified by un-ligated first primer. Using a microfluid array, an SNP in a target sequence of nucleic acid can be thus be advantageously identified. In various embodiments, a kit may be provided that includes the microfluidic array chip, primer sequences, and reagents required to selectively ligate primers for amplification of a desired target nucleic acid sequence.

Alternatively, the encapsulated components could be an array of samples for probing with one or a few assays; for example, immobilized patient DNA samples for use in epidemiological studies. In some cases, the entire array could have the sample immobilized assay system which may be used, for example, in haplotyping by limiting dilution PCR. For some applications it may be desirable to combine both genotyping and RNA expression analysis assays in the same array which may be advantageous for sample tracking as in for patient samples.

It is important to note that simply drying the reagents onto the walls of the through-holes without an encapsulating matrix would be problematic in that if the sample is loaded by dipping of the array, dragging of droplets across the array, or other method that exposed the sample to multiple through-holes simultaneously, the reagents may dissolve and contaminate neighboring channels as well as reduce the reliability of results in the channels that lost material. This is of especially high importance is target molecules are array as for studies of patient populations since target molecules are amplified by PCR whereas primers and probes are not. A means for reducing this crosstalk may be implemented in the array such as adding a second layer of protective wax. The composition of this second layer may be the same as for the first layer, or may differ.

For many assays, it is important that the interior surfaces of the through-holes (the walls) are biocompatible so that they do not interfere with the reaction by adsorbing, denaturing, reacting with or catalytically destroying the assay components. For this reason, it is preferable to coat the walls with a biocompatible material. This material could be for example, a covalently linked PEG bearing silane. This coating should be thermally stable at the highest temperatures used in the assay (typically 95° C. for PCR).

In order to increase the sensitivity of the assay a sequence capture-PCR array may be created. The through-holes of an array 72, such as the one shown in FIG. 7, may be provided with an array of sequence specific hybridization capture probes, in accordance with one embodiment of the invention. The probes may be, without limitation, immobilized on the interior walls of the array 72, or on a porous material embedded within the throughholes. A sample containing a nucleic acid to be amplified is allowed to hybridize to the probes as is common for hybridization arrays. The array 72 may be washed in a buffer designed to remove non-specifically bound nucleic acids. PCR reagents are then introduced into the sample array 72 by stacking with a second through-hole array or by other means. For example, the second array may contain primers that specifically amplify the sequence complementary to the probes, or may contain universal primers. Thermal cycling and analysis can then be performed. More detail on adapting the through-holes of the array 72 for functional processing of a sample, and stacking of arrays 72, is provided in the section below.

In one specific embodiment, the array 72 may include at least three different reagent oligonucleotides: (1) a capture probe oligo immobilized on the through-hole wall having a high specificity for the target DNA, and (2) a forward PCR primer and (3) a reverse PCR primer for amplification of the target DNA. Such an approach provides high specificity for the target DNA based on three different domains of specificity that must be met.

The advantages of such embodiments include a reduction of template sample mass requirements by greater than 10-fold (greater than 100-fold in some embodiments), and increased specificity of the output by combining specific hybridization with the specificity inherent in the PCR sequencing. Similar embodiments are also compatible with techniques other than PCR, such as DNA sequencing or non-thermal amplification systems.

Single and Multi-Functional Assays

In illustrative embodiments of the invention, individual through-holes of the sample array are adapted for single or multi-functional processing of a liquid sample. Single or multi-functional processing may include the capture of one or more targets of interest and/or chemical processing of the captured targets. The target capture may be based on a nucleic acid probe, protein antibody, aptamer or other capture agent of material immobilized within the through-holes. The chemical processing may use immobilized reagents that serve to modify the captured targets.

In one embodiment, the chemical processing includes amplifying and detecting a signal from the captured targets. For example, the chemical processing may utilize encapsulated TaqMan® PCR reagents, or reagents for some other nucleic acid detection scheme. In some embodiments, the chemical processing may be specific to the captured targets. For example, the target capture can use oligonucleotides immobilized within the through-holes to specifically capture target nucleic acids in a sample, such as by a stringent hybridization. The chemical processing then may use TaqMan® reagents with primers and probes specific to the target nucleic acids captured by the immobilized oligonucleotides.

The assay reagents such as primers, molecular probes, proteins, antibodies, enzymes, enzyme-antibody conjugates, nucleotides, oligonucleotides, fluorimetric substrates, buffers, salts, blocking agents, or some other assay component can be immobilized within the through-holes in a variety of manners so as to release the substances upon activation into aqueous solution within the sample through-hole. Activation may be triggered, for example, via prolonged incubation or by exposure to heat, light, solvent, pH, oxidant, reducing agent, or some other trigger. These immobilization techniques include covalent attachment, non-covalent attachment, and immobilization in a material with good surface adherence properties such as polyethylene glycol (PEG). Hereinafter such materials will be referred to as waxes. Preferentially, the wax should be hydrophilic to facilitate loading of the through-holes by use of surface energy. The wax should also be biocompatible so as not to interfere with the reaction or detection system. In some applications, the chip may be exposed to elevated temperatures (e.g., around 40° C.) for several hours, and thus the wax may need to have a higher melting point (or be sealed-in with a layer of high-melting wax).

Assay reagents such as probes and primers may be mixed with wax and transferred from reagent stocks in microplates into the sample through-holes in the multi-functional chip, for example by use of a high-accuracy robotic pin tool. The prepared chips are then dried to immobilize reagents such as PCR primers and probes on the walls of the sample through-holes. If the wax is hydrophilic, a solution containing a target of interest such as a patient's DNA and a polymerase (such as Taq) along with other reagents needed for PCR can be loaded into the through-holes by dipping or other means, as described above. Upon thermal cycling, the wax will melt and dissolve, releasing the nucleic acid component.

In some embodiments, multiple reagents are dried in multiple layers of wax within the through-holes. FIG. 24(a) shows a through-hole 240 having an outer first layer of wax 241 displaying target capture reagents, and an inner second layer of wax 242 having chemical process reagents. FIG. 24(b) shows an alternative embodiment in which the first layer of wax 241 and the second layer of wax 242 are attached to the interior walls of the through-hole 240 at different locations. In either embodiment, each layer of wax may have different melting temperatures (e.g., different polymer lengths) to allow sequential activation of these reagents at different temperatures. In FIG. 24(a), this would mean that outer first layer of wax 241 would have a lower melting point than the inner second layer of wax 242. This can be easily accomplished simply by applying and drying the lower melting point wax after the higher melting point one.

In some embodiments, the double layer wax structure may be present in only a selected subset of the through-holes in order to enable multiple types of analysis such as RNA and DNA analysis or ELISA and PCR analysis on the same chip. In other words, the immobilized reagents can vary from through-hole to through-hole to provide multiple types of information (e.g., SNP, gene expression patterns, etc.) on one or more samples.

Such a layered wax chip is useful, for example, for a two-step reverse transcription/PCR system in which the reverse transcription copies sample RNA to DNA, and then PCR processing amplifies the DNA as for detection, such as by Quantitative PCR (QPCR)). The required PCR primers and probes are dried down in the sample through-holes first in wax that melts at 65° C. Then primers for the reverse transcription reaction are dried over the first wax layer in a second top layer of wax that melts at 45° C.

The RNA sample (such as from an RNA virus) along with a one-tube RT-PCR master mix with a thermostable reverse transcriptase (available, for example, as SuperScript™ from Invitrogen Corporation of Carlsbad, Calif.) can then be added and heated up to 50° C. to release the reverse transcription primers and then incubated at 37° C. to allow the reverse transcriptase reaction to occur. The maximum temperature used in various applications can vary within the temperature stability limits of the enzyme. Then the chip is thermally cycled to release the PCR primers and probes and perform the PCR amplification and analysis. An additional level of specificity may be gained in the assay by using different probes for the RT and corresponding PCR. This technique can also be used in other sorts of assays where time or temperature sequential addition of reagents is required.

Layers of multiple melting point waxes may also be useful for reducing sample cross-talk (cross-contamination) that might result from immobilized nucleic acids traveling to nearby through-holes, such as during the sample dipping/loading process. This may involve an outer protective layer of wax that shields the lower layer(s) of wax. This protective layer of wax could be the same or different composition as the underlying layer(s).

Layered wax embodiments provide great design flexibility. For example, the target capture process need not have nucleic acid probes, but could be used to isolate viral particles directly as by affinity capture with immobilized antibodies. The chip is then washed and the nucleic acids are released by heat, lytic enzymes, or other means. If further purification, specificity, or nucleic acid stability is needed, oligo-capture probes may be mixed with the antibody capture probes. In this case, an on-chip reverse transcription reaction is necessary: Lytic enzymes may be chosen to denature upon heating and thus not affect the reverse transcriptase or polymerase needed for PCR.

In various embodiments, multiple functionalities may be integrated into a multifunctional chip by producing multiple chips containing complementary reagents. Then, two (or more) chips can be layered together to form a single integrated multi-functional chip. Some embodiments may start by bonding separate dedicated capture and chemical processing chips such that the chemical processing functionalities in the through-holes of the chemical processing chip will align with the appropriate capture functionalities in the capture chip. In some embodiments, it may be possible to mix the capture and chemical processing functionalities between the two chips as long as the correspondence between the capture and chemical processing functionalities is maintained.

Figure 25:
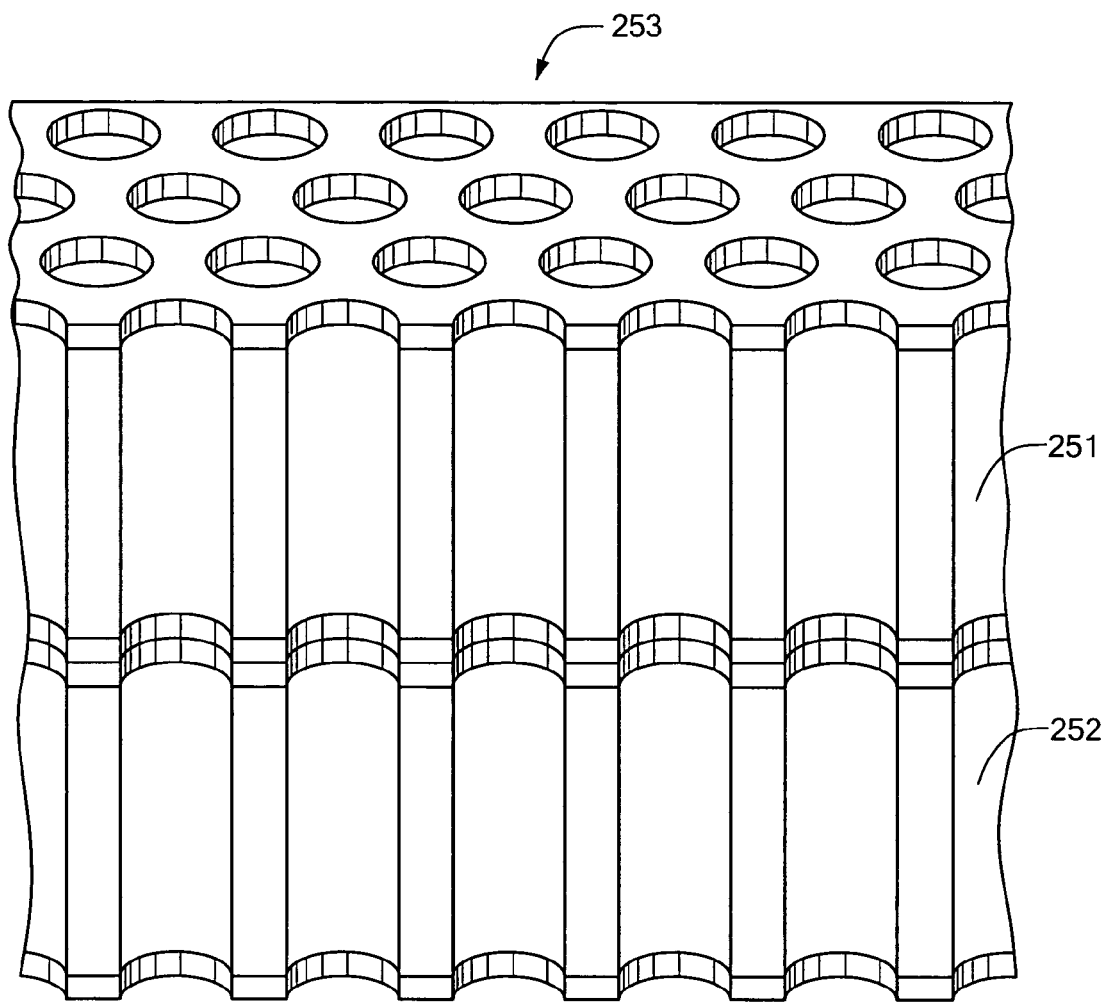
FIG. 25 is a diagram illustrating a layered microfluidic array structure, in accordance with an embodiment of the invention.

FIG. 25 shows an embodiment in which a top chip layer 251 is stacked directly onto a bottom chip layer 252. Although FIG. 25 shows two different chip layers, other embodiments could have three or more chip layers. The chip layers are aligned so that the through-holes in each are aligned together, and the two chip layers 251 and 252 are fixedly connected to each other to form a single unified layered structure 253. Multiple chip layers 251 and 252 can be attached to each other in various apparent ways such as by use of adhesives, chemical cross linkers, screwing, bolting, riveting, clamping, etc. Or if the surfaces of the chip layers 251 and 252 are polished or sufficiently flat, they may be bonded directly using pressure or by use of Van Der Waals forces.

Many different nucleic acid component sets such as sets of hybridization probes and PCR primers can be preloaded into the layered chip in this way for rapid analysis. The loading of the nucleic acid component or samples to be analyzed may be accomplished in various ways such as by pipetting a solution containing the nucleic acid component directly into the sample through-holes, or by dragging a drop of solution containing the nucleic acid component over the openings of the sample through-holes. Or, the chip layer can be dipped in a solution containing the nucleic acid component, and then withdrawn. Alternatively, arrays of nucleic acid targets as might be obtained from numerous patient samples may be immobilized and then loaded with reagents such as PCR master-mix containing primers and probes. Once a total number of DNA detection assays is established for a given specific application, the number of through-holes may be reduced to minimize non-specific binding by the unused through-holes. The openings of unused through-holes may be blocked with wax to prevent non-specific binding of the sample target DNA.

For example, such a layered chip may provide DNA capture and amplification in which one chip layer captures DNA of interest in a liquid sample onto an array of oligonucleotides covalently linked to the hydrophilic surfaces of the through-holes, while another chip layer amplifies the captured DNA such as by PCR.

The PCR primers and probes encapsulated in the array of through-holes of the second chip layer may be specific for the targets captured by the oligonucleotides in those through-holes. In an example diagnostic assay, this enables multiple assays per pathogen against numerous pathogens and replicate analyses to increase data quality. The flow-through nature of such a multi-functional chip may be used to facilitate target concentration, purification, and amplification, which increases nucleic acid detection sensitivity by as much as an order of magnitude or more compared to previous nucleic acid analysis methods. Some embodiments could have a combination of multiple chip layers as well as one or more layers of reagent-bearing wax such as described above.

In a DNA capture and amplification embodiment, the capture chip layer has specific nucleic acid probes (e.g. 40-60 mers of DNA) attached to the sides of the sample through-holes. Robust interior oligonucleotide-capture surface coatings may be used consistent with the goal of minimizing non-specific binding. Established chemistries for immobilizing oligonucleotides onto surfaces may be exploited. For example, oxide surfaces (such as glass) may be modified with undecenyltrichlorosilane to produce a monolayer exposing a vinyl group carboxylate at its end, which is functionalized to carboxylic acid by exposing to $KMnO_4/NaIO_4$ in aqueous solution. The carboxylic acid is activated to NHS ester by subsequent exposure to 1-Ethyl-3-(3-dimethylanomipropyl) carbodiimide hydrochloride (EDC) and N-hydroxysuccinimide (NHS) ester. Oligonucleotides or cDNA strands bearing an amine group at its end could then be immobilized to the surfaces by forming amide bonds via the reaction between NHS ester on the surface and amine group in the strands. The amide bond and underlying undecenyltrichlorosilane monolayer are expected to provide sufficiently robust linkage to retain the strands on the surface under hybridization conditions.

The different chip layers should be mechanically bound together in precision alignment so that the through-holes containing complementary PCR primers and hybridization probes in each layer are aligned. A hermetical bond may be desirable but is not necessarily needed provided that the chip layer surfaces in contact are hydrophobically coated. In this case, the layer bonding process also should not modify the coating hydrophobicity to ensure fluidic isolation between adjacent through-holes. In one specific embodiment, the two chip layer exterior faces are pre-coated with reactive monolayers prior to filling with assay probes, then bonded together by catalyst-activated crosslinking.

If adhesives are applied after the probes are added, or after the hybridization step, then the adhesive application process should minimize spillover into the through-holes since adhesives may inhibit PCR or bind target oligos. Excess adhesives may be washed away from the through-hole interiors with solvents that do not dissolve the encapsulating wax. The bonding process should also work near room temperature so as not to melt any probe-encapsulation wax, and should ideally be done in a manner that does not contaminate the chip with dirt or nucleic acid contaminants (though washing is possible). This may require testing of different pressure sensitive adhesives and dispensing mechanisms such as sprayers, rollers and stamps to develop a means of applying uniform pressure. Alignment can be accomplished by the use of a precision jig having pins complementary to guide holes that are precision etched during the chip layer manufacturing process. If needed, chips can be blocked with a blocking agent such as bovine serum albumin (BSA) to occupy any binding sites created in the bonding process. Hybridization buffers and PCR master mix may be formulated with dynamic blockers to improve their compatibility with the adhesive layer.

The capture chip layer works in a manner similar to a standard glass-slide spotted hybridization array—nucleic acids may be diluted in a buffer designed to optimize speed and/or specificity of hybridization and have a chance to visit all of the sample through-holes of the capture chip layer and thus come to a low free-energy state of complementary hybridization. Alternatively, the hybridization may occur in a crude or diluted patient sample such as a nasopharyngeal wash sample. Enzyme may be used to disrupt pathogens prior to hybridization.

The capture chip layer may be incubated with a nucleic acid sample for 6 hours or more as with a standard microarray. This incubation time may be reduced by circulating sample through and around the chips, but the wax encapsulation matrix encasing the PCR primers and probes needs to resist dissolution until the thermal cycling is initiated by heating to 95° C. Additionally, stringency can be controlled by lowering salt concentrations, resulting in lower incubating temperatures. In some applications there may be two additional options: (1) decrease the hybridization temperatures and sacrifice specificity of hybridization and possibly limit detection, or (2) manually stack the chip with amplification reagents onto the capture chip after the hybridization step. Manual stacking methods have been described in U.S. patent application Ser. No. 09/850,123, entitled "Methods for Screening Substances in a Microwell Array," filed May 7, 2001, which is herein incorporated by reference. Manual stacking may involve, for example, the steps of stacking at least two platens together in such an adjacent manner that at least one of the plurality of through-holes from each platen is registered with a through-hole of each other adjacent platen so as to form at least one continuous channel, and transferring the liquid into each continuous channel. Each platen may be separated from each adjacent platen by an air gap, and the liquid may be transferred with capillary tubes or at least one cannula.

Hybridization reaction kinetics are diffusion-rate limited and given that the diffusion constant for nucleic acids is small ($\sim 10^{-6}$ cm$^2$/s), diffusion into or within the through-holes may not be enough for rapid hybridization. This problem may be addressed by increasing the surface capture area within each through-hole such as by actively circulating sample to repetitively force it through the capture chip layer. Surface capture area can also be increased by introduction of a porous matrix into each through-hole that can be functionalized with hybridization capture probes. Matrix porosity should be selected to maximize surface area while minimizing the pressure required for liquid flow through the through-holes. For example, porous glass may be synthesized in the through-holes by filling the through-holes with a mixture of potassium silicate mixed with formamide, and then baking at 110° C. for one hour. By varying the concentration of formamide or including particles such as porous silica or polymer beads in the potassium silicate mix, the porosity of the matrix can be adjusted as desired. Furthermore, immobilization chemistry as described herein can be used to attach capture probes to the glass surface. In other embodiments, alternatives such as polyacrylamide, agar or aero gels can be used.

To increase hybridization rates, the chip can be spun/rotated (see, for example, FIGS. 16(a-b). Alternatively, agitating the sample with surface acoustic waves using the ArrayBooster™, a commercially available hybridization instrument from Advalytix, can accelerate hybridization rates as well.

The amplification chip layer has probes and primers for PCR that are appropriate to assay the nucleic acids that the corresponding sample through-holes in the capture chip layer capture. For example, the probes can be designed to capture a particular viral genome or genome fragment and the PCR reagents can amplify one or more sequences within that genome. In a DNA capture and amplification embodiment using wax immobilized reagents, the captured oligo-target nucleic acid pair will melt upon initiation of thermal cycling and the amplification chip layer may have primers that either overlap the capture sequence or are independent. Such an embodiment greatly saves on reagent costs. For example, a standard tube of TaqMan® PCR reagent enables approximately 150,000 tests in such chips.

Use of a prepared layered chip starts with preparation of nucleic acid samples using standard methods of purification and modification. For example, after lysing any potential microbes, the user could use a Qiagen RNA/DNA kit to extract the genomic material, split the sample and perform a random hexamer primed reverse transcription (RT) on a sample fraction, then recombine the two samples. In some embodiments, the RT may be performed on a small fraction of the original sample since viral RNA tends to be present in much higher titers than bacterial DNA.

As in above-described embodiments, the layered chip can be loaded with the prepared sample in a variety of ways. For example, a volume of high-density encapsulation fluid can be added to a chip holder case that is open on one side. The nucleic acid sample may then be floated in a thin layer on top of the encapsulation fluid. The prepared chip is then lowered into the chip holder case, and self-loaded with sample as it passes through the sample layer into the encapsulation fluid. The chip holder case may then be sealed, such as by a sealant that is dispensed on top of the sample and cured.

The capture probes in one of the chip layers, e.g., top chip 31, will interact with and capture the target nucleic acid in the sample liquid. After washing in a buffer to remove non-specifically bound nucleic acids and then replacing the wash buffer with a PCR master-mix (a solution that typically contains polymerase, nucleotides, buffers, magnesium chloride, and dynamic blockers), the layered structure 33 is placed in a thermal cycling system, where elevation of temperature to start a PCR process melts the PEG in the other chip layer, e.g., bottom chip 32, releasing PCR primers and/or probes to commence PCR amplification of the target nucleic acid captured in the through-holes of the other chip.

Imaging/analysis can then be performed on the chip, either in combination with or separately from the thermal cycling processing. Although nucleic acids could alternatively be detected in the chip using end-point PCR, quantitative PCR offers compelling advantages for some applications. After thermal cycling and analysis, the used chip holder case containing the PCR chip and sample can be disposed of.

A complete system to an end-user might include hermetically sealed layered chips that are pre-loaded with capture and PCR primers, along with dilution buffers and master mix, a chip loading and sealing solution, and a compact, inexpensive imaging thermal to cycler for real-time PCR. One specific product is based on a 1"×3" microscope slide-format array chip for use in genotyping by PCR based on end-point analysis. The consumables include a 3072-hole chip and chip case, along with master mix and sealing reagents (perfluorinated liquid and UV curable sealant). With an auto-loading slide scanner and a 20-slide flat block thermal cycler costing less than $100,000, 30,000 SNP analyses per hour can be performed. This is an order of magnitude lower on a SNP per day basis than other systems presently offered, with the added advantage of lower sample consumption.

A layered chip structure can be useful in a variety of other specific applications, for example, detecting a pathogen in a clinical sample. One chip layer can be arranged to capture the target pathogen with an antibody, which may be immobilized on the interior, hydrophilic surface of the chip, and the other chip layer can be arranged for detection of the captured pathogen by PCR amplification. Lysis enzymes such as lysozyme, lipase, or zymolase can be immobilized in wax to aid in lysis of the captured pathogen.

One of the problems with enzyme linked immunosorbant assay (ELISA) arrays is that they currently need to have common assay conditions. A layered chip structure as described above can overcome that, and can also be useful for varying the conditions of ELISA by immobilizing reagents such as buffer salts in wax within one of the chip layers. An ELISA approach may be used in which the pathogen is captured by an antibody immobilized in one part of the through-hole, and a detection antibody is encapsulated in a low-melting point PEG in another part of the through-hole and slowly released into solution. The chip is then rinsed to remove non-bound detection antibodies and the ELISA is developed with secondary antibody conjugated to an enzyme such as alkaline phosphatase or horseradish peroxidase and detected by washing and adding any of the several available chromogenic, flourogenic, or luminescent substrates.

In other examples, capture chip layers can be loaded with DNA hybridization probes for viral RNA and bacterial DNA found in pathogens such as SARS, Influenza A, Influenza B, Respiratory Syncytial Virus, Parainfluenza-1, Parainfluenza-2, Parainfluenza-3 and *Bacillus anthracis*. Complementary amplification chip layers are then loaded with dry, encapsulated TaqMan® primers and probes to viral nucleic acids sequences expected to be present in the captured viral nucleic acids. The chip layers are bonded and tested for several parameters: detection limits, specificity, quantitative accuracy, chip to chip variability, day to day variability over several months, user to user variability.

While embodiments based on offline sample preparation with oligonucleotide capture and PCR amplification described above are useful in their own right, further embodiments go directly from patient sample to end results with a minimum of operator dependent steps. For example, in one embodiment, multiple viruses can be captured by antibodies in one chip layer, the viruses can be disrupted by temperature and/or enzymatic digestion (while protecting the viral nucleic acids from degradation), and then the lytic enzymes can be denatured (e.g., thermally) and reverse transcription-PCR can be performed. Such an embodiment avoids the need for standard nucleic acid sample-preparation procedures.

Thus, embodiments of the present invention include a reverse transcription system and a PCR amplification system that is encapsulated in multiple chip layers to create an integrated RT-PCR array. Various embodiments also are able to detect low concentrations of multiple pathogen nucleic acid sequences. Specific embodiments also incorporate multiple existing PCR assays for detection of respiratory pathogen nucleic acids including SARS RNA.

Embodiments also provide high test specificity. For example, three probes can be provided for each target DNA sequence; two PCR primers and a capture probe consisting of a complimentary sequence. In some cases, a fourth probes such as a Taqman® probe or molecular beacon may also be used. This reduces the occurrence of false positives and false negatives. Thus, the ability to perform PCR in a high density microfluidic array format can provide superior data quality as compared to conventional DNA microarrays. Additionally, multiple sequences per pathogen can be easily assayed to further increase reliability and decrease the consequences of pathogen mutation.

In addition, specific embodiments have the ability to detect multiple pathogens. By performing reactions in parallel, one-pot multiplex reagents do not have to be developed. Conventional multiplexing either makes use of multiple dyes, which usually allows the detection of just two or three sequences, or a post-processing step such as electrophoresis which adds cost and complexity.

Furthermore, embodiments are well-suited for point-of-care use. The low cost, compact size, and ease of use of specific embodiments enables multiplexed PCR-based assays to be performed in many clinical and point-of-care settings. The greatly reduced primer and probe volumes and the low cost materials and processing methods that have been developed enable a low cost solution for widespread use.

Embodiments are also very scalable, to permit performing a smaller or larger number of measurements per patient sample and/or to process multiple patient samples in parallel. Specific embodiments support chip formats containing up to 24,576 probes or samples. Multiple layered chips can be processed in parallel in a manner analogous to conventional DNA microarrays. Advanced concepts for capture/hybridization may simplify upstream purification processes and enable future integrated devices.

Once produced, layered structure chips typically will be packaged and stored for a reasonable amount of time—perhaps several months—depending on the overall chip format such as the presence of encapsulated proteins and antibodies. Formulations with various stabilizers such as sugars and anti-oxidants may be beneficial. Vacuum packaging and packaging in inert gas with various moisture contents could also be useful, as could cold or frozen storage.

Although various exemplary embodiments of the invention have been disclosed, it should be apparent to those skilled in the art that various changes and modifications can be made which will achieve some of the advantages of the invention without departing from the true scope of the invention.

What is claimed is:

1. A system for analyzing a PCR reaction, comprising:
a sample holder comprising a plurality of reaction volumes configured to receive a corresponding plurality of samples, each reaction volume having a volume of less than 100 nanoliters, the reaction volumes being spatially separated from one another;
a case comprising a case volume and an opening, the case configured to contain the sample holder within the case volume, the opening configured for dispensing a liquid into the case volume;
an imaging system comprising an illumination source, the imaging system configured to image the plurality of samples; and
a processor comprising analysis software configured to perform an end-point PCR analysis on at least some of the plurality of samples;
wherein the sample holder comprises a sheet of material comprising a pair of opposing surfaces, the plurality of reaction volumes comprises a plurality of through-holes, and the plurality of through-holes are disposed between the opposing surfaces.

2. The system of claim 1, wherein the illumination source is configured to simultaneously illuminate an entirety of the reaction volumes.

3. The system of claim 1, wherein the illumination source comprises a light emitting diode.

4. The system of claim 1, wherein the end-point PCR analysis comprises genotyping.

5. The system of claim 1, wherein the reaction volumes have a density greater than one reaction volume per 0.25 $mm^2$.

6. The system of claim 1, wherein the sample holder comprises at least 3072 reaction volumes, the plurality of samples being disposed within respective ones of the 3072 reaction volumes.

7. The system of claim 1, further comprising a thermal cycler configured to cycle the plurality of samples over a temperature range.

8. The system of claim 1, wherein the system further comprises a liquid, wherein the liquid comprises at least one of a mineral oil, a silicon oil, or a perfluorinated hydrocarbon.

9. The system of claim 1, wherein the analysis software is configured to perform a quantitative PCR.

* * * * *